(12) United States Patent
Okamura et al.

(10) Patent No.: US 8,916,316 B2
(45) Date of Patent: Dec. 23, 2014

(54) REFLECTING MASK BLANK, METHOD FOR MANUFACTURING REFLECTIVE MASK BLANK AND METHOD FOR QUALITY CONTROL FOR REFLECTIVE MASK BLANK

(71) Applicant: Asahi Glass Company, Limited, Chiyoda-ku (JP)

(72) Inventors: Yuzo Okamura, Tokyo (JP); Yoshiaki Ikuta, Tokyo (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 14/196,572

(22) Filed: Mar. 4, 2014

(65) Prior Publication Data

US 2014/0186753 A1 Jul. 3, 2014

Related U.S. Application Data

(63) Continuation of application No. PCT/JP2012/071905, filed on Aug. 29, 2012.

(30) Foreign Application Priority Data

Sep. 1, 2011 (JP) ................................. 2011-191057

(51) Int. Cl.
*G03F 1/24* (2012.01)
*G03F 1/44* (2012.01)
*G01B 11/14* (2006.01)
*G01B 15/00* (2006.01)
*G01N 21/95* (2006.01)

(52) U.S. Cl.
CPC .. *G03F 1/24* (2013.01); *G03F 1/44* (2013.01); *G01B 11/14* (2013.01); *G01B 15/00* (2013.01); *G01N 21/95* (2013.01)
USPC .................................... 430/5; 430/22; 430/30

(58) Field of Classification Search
CPC ..................................... G03F 1/24; G03F 1/44
USPC .................................................. 430/5, 22, 30
See application file for complete search history.

(56) References Cited

U.S. PATENT DOCUMENTS

| 7,660,456 | B2 | 2/2010 | Ishida et al. | |
|---|---|---|---|---|
| 8,399,833 | B2 * | 3/2013 | Yoshitake | ..................... 250/307 |
| 2010/0178597 | A1 | 7/2010 | Ishida et al. | |
| 2010/0237256 | A1 | 9/2010 | Yoshitake | |
| 2011/0217634 | A1 | 9/2011 | Shoki | |
| 2012/0019916 | A1 | 1/2012 | Shoki | |
| 2013/0078555 | A1 * | 3/2013 | Orihara et al. | ..................... 430/5 |
| 2014/0011123 | A1 | 1/2014 | Okamura et al. | |

FOREIGN PATENT DOCUMENTS

| JP | 11-176728 | 7/1999 |
|---|---|---|
| JP | 3412898 | 3/2003 |
| JP | 2010-79112 | 4/2010 |
| JP | 2010-219445 | 9/2010 |
| WO | 2008/129914 | 10/2008 |
| WO | 2010/061725 | 6/2010 |
| WO | 2010/110237 | 9/2010 |

OTHER PUBLICATIONS

International Search Report issued Oct. 2, 2012 in PCT/JP2012/071905 filed Aug. 29, 2012.
International Symposium on Extreme Ultraviolet Lithography, S. Huh et al., "Printability and Inspectability of Programmed and Real Defects on the Reticle in EUV Lithography" 2010.
EUVL Mask Fiducial SEMI Standard Discussion Jan. 2006, P. Seidel and P.Y. Yan.

\* cited by examiner

*Primary Examiner* — Christopher Young
(74) *Attorney, Agent, or Firm* — Oblon, Spivak, McClelland, Maier & Neustadt, L.L.P.

(57) ABSTRACT

The present invention relates to a reflective mask blank containing in this order, a substrate, a multilayer reflective film that reflects exposure light, and an absorber layer that absorbs the exposure light, in which the reflective mask blank further contains a fiducial mark indicating a reference position of the multilayer reflective film, which is formed in a concave shape or in a convex shape on a surface of the multilayer reflective film or on a surface of one layer formed between the multilayer reflective film and the absorber layer, and the fiducial mark is formed so as to have a reflectivity different from an area surrounding the fiducial mark with respect to a light with a prescribed wavelength and is transferred to a layer formed on the fiducial mark.

20 Claims, 8 Drawing Sheets

REFLECTING MASK BLANK, METHOD FOR MANUFACTURING REFLECTIVE MASK BLANK AND METHOD FOR QUALITY CONTROL FOR REFLECTIVE MASK BLANK

TECHNICAL FIELD

The present invention relates to a reflective mask blank, a method for manufacturing reflective mask blanks, and a method for quality control for reflective mask blanks.

BACKGROUND ART

Recently, for enabling transfer of micropatterns having a size of 40 nm or less, EUV exposure technology has become considered to be a promising one in place of existing ArF exposure technology that uses ArF excimer laser light having a wavelength of 193 nm. In EUV exposure technology, used is EUV (Extreme Ultra-Violet) light having a shorter wavelength than ArF excimer laser light, as the exposure light therein. Here, the EUV light includes soft X-ray and vacuum UV light, and is concretely light having a wavelength of from 0.2 to 100 nm or so. At present, as the exposure light, EUV light having a wavelength of 13.5 nm or so is mainly investigated.

In EUV lithography (EUVL) technology, a reflective photomask is used. The reflective photomask comprises a multilayer reflective film and an absorber layer as formed in this order on a substrate, in which a part of the absorber layer is removed. The absorber layer is formed in a prescribed pattern. EUV light incident on the reflective photomask is absorbed in area where the absorber layer exist but is reflected by the multilayer reflective film in the other area where the absorber layer does not exist whereby an image is formed on the surface of the exposed material by an optical system. In that manner, the pattern of the absorber layer is transferred to the surface of the exposed material.

The multilayer reflective film has a periodical structure of some types of layers each having a different refractive index and repeatedly stacked on a substrate in a prescribed order. For example, the multilayer reflective film comprises, as stacked alternately and repeatedly therein, Mo layers as low-refractivity layers and Si layer as high-refractivity layers.

In cases where the multilayer reflective film is contaminated with foreign substances during stacking thereof, or in cases where defects (e.g., foreign substances, flaws, pits) exist in the surface of the substrate on which the multilayer reflective film is formed, the periodical structure of the multilayer reflective film would be disordered to give defects (so-called phase defects) in the multilayer reflective film. Such defects, if formed, would bring about a problem in that the pattern of the reflective photomask could not be faithfully transferred to a wafer. Technically, it is extremely difficult to absolutely remove the defects from the multilayer reflective film (e.g., see Non-Patent Document 1).

Given the situation, investigated is a technique of controlling the position and the direction of the pattern of the absorber layer in accordance with the position of the defects in the multilayer reflective film (e.g., see Non-Patent Document 2).

In addition, for accurately identifying the position of the defects in the multilayer reflective film, there is proposed a technique of previously forming a fiducial mark on the surface of the substrate on which the multilayer reflective film is formed (e.g., see Patent Document 1). The fiducial mark is transferred to the multilayer reflective film, and based on the position of the transferred fiducial mark as the reference position, the position of the defects in the multilayer reflective film can be identified.

Apart from the above, there is also proposed a technique of correcting the defects in the multilayer reflective film by identifying the position of the defects in the multilayer reflective film (e.g., see Patent Document 2). Patent Document 2 says that, when an absorber layer is formed on the multilayer reflective film therein, a fiducial mark is formed on the absorber layer but is not formed on the substrate nor the multilayer reflective film.

CITATION LIST

Patent Literature

Patent Document 1: WO10/110,237
Patent Document 2: WO08/129,914

Non-Patent Literature

Non-Patent Document 1: 2010 International Symposium on Extreme Ultraviolet Lithography, S. Huh et al., "Printability and Inspectability of Programmed and Real Defects on the Reticle in EUV Lithography"
Non-Patent Document 2: EUVL Mask Fiducial SEMI Standard Discussion January 2006, P. Seidel and P. Y. Yan

SUMMARY OF THE INVENTION

Problems that the Invention is to Solve

The position of the defects in a multilayer reflective film can be identified with reference to the position of the fiducial mark as the reference position. Regarding conventional fiducial marks, the reproducibility of the detected position with inspection light is not sufficient and therefore it has been difficult to accurately identify the position of defects, based on the position of the fiducial mark as the reference position.

The present invention has been made in consideration of the above problems, and is intended to provide a reflective mask blank capable of accurately identifying the position of the defects in the blank, especially the defects in the multilayer reflective film therein, to provide a method for manufacturing reflective mask blanks, and to provide a method for quality control for reflective mask blanks.

Means for Solving the Problem

In order to solve the above problems, the reflective mask blank according to one aspect of the present invention is a reflective mask blank containing in this order, a substrate, a multilayer reflective film that reflects exposure light, and an absorber layer that absorbs the exposure light, in which the reflective mask blank further contains a fiducial mark indicating a reference position of the multilayer reflective film, which is formed in a concave shape or in a convex shape on a surface of the multilayer reflective film or on a surface of one layer formed between the multilayer reflective film and the absorber layer, and in which the fiducial mark is formed so as to have a reflectivity different from an area surrounding the fiducial mark with respect to a light with a prescribed wavelength, and is transferred to a layer formed on the fiducial mark.

Further, the method for producing a reflective mask blank according to another aspect of the present invention is a method for producing a reflective mask blank containing in this order, a substrate, a multilayer reflective film that reflects exposure light, and an absorber layer that absorbs the exposure light, the method containing:

a step of forming a concave-shaped or convex-shaped fiducial mark indicating a reference position of the multilayer reflective film on a surface of the multilayer reflective film or on a surface of one layer formed between the multilayer reflective film and the absorber layer, in which the fiducial mark is formed so as to have a reflectivity different from an area surrounding the fiducial mark with respect to a light with a prescribed wavelength, and is transferred to a layer formed on the fiducial mark.

Furthermore, the method for quality control for a reflective mask blank according to another aspect of the present invention is a method for quality control for a reflective mask blank described in the above one aspect, the method containing:

a step of identifying a position of a defect of the multilayer reflective film based on a position of the fiducial mark as a reference position, after formation of the multilayer reflective film and before formation of the absorber layer.

Effect of the Invention

According to the present invention, there are provided a reflective mask blank capable of accurately identifying the position of the defects in the multilayer reflective film, a method for manufacturing reflective mask blanks, and a method for quality control for reflective mask blanks.

MODE FOR CARRYING OUT THE INVENTION

Embodiments of the present invention are described below with reference to the drawings, in which the same or the corresponding reference signs are given to the same or the corresponding configurations and the description thereof is omitted.

In the following embodiments, a reflective mask blank for EUVL is described; however, the present invention is applicable to any reflective mask blank that uses light having a wavelength except EUV light as the exposure light.

First Embodiment

Figure 1:
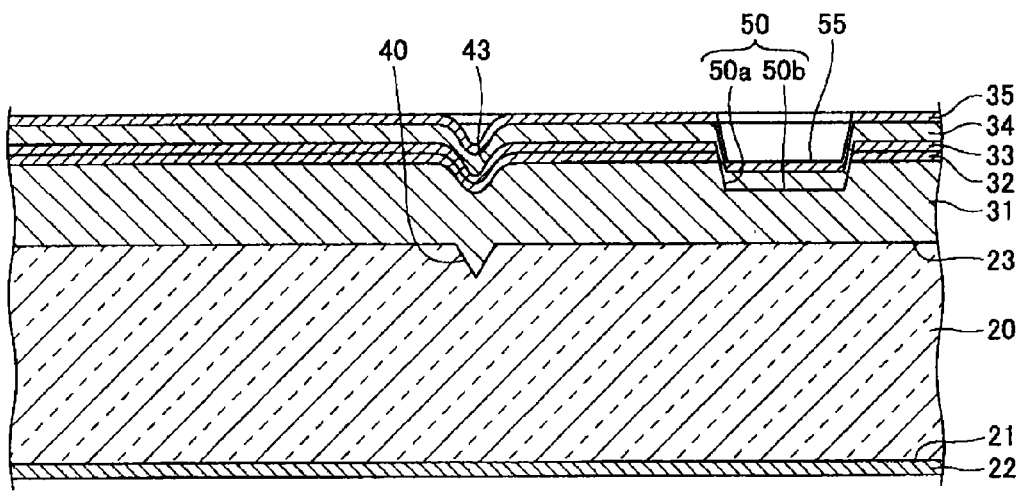
FIG. 1 is a cross-sectional view of a reflective mask blank according to the first embodiment of the present invention.
Figure 2:
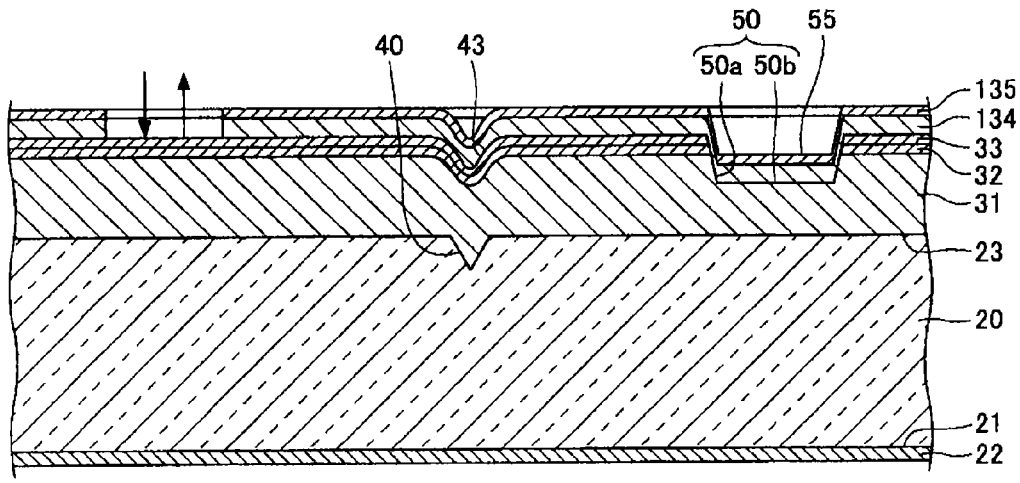
FIG. 2 is a cross-sectional view of one example of a reflective photomask produced by removing a part of an absorber layer of a reflective mask blank.

FIG. 1 is a cross-sectional view of a reflective mask blank according to the first embodiment of the present invention. FIG. 2 is a cross-sectional view of one example of a reflective photomask produced by removing a part of an absorber layer of a reflective mask blank.

The reflective mask blank 10 contains, as formed on the substrate 20 in this order, a multilayer reflective film 31 that reflects EUV light, a protective layer 32 that protects the multilayer reflective film 31, a buffer layer 33 for patterning, an absorber layer 34 that absorbs EUV light, and a low-reflection layer 35 of which the reflectivity to inspection light is lower than that of the absorber layer 34.

Here, the protective layer 32, buffer layer 33 and low-reflection layer 35 are optional configurations and may be omitted. In addition, the reflective mask blank 10 may have any other functional layer.

The reflective mask blank 10 is patterned according to an ordinary mask production process to be a reflective photomask 100. For example, a resist film is formed by coating on the surface of the reflective mask blank 10, then heated and thereafter an image is drawn by electron beams or UV rays. In this stage, the position and the direction of the drawing pattern is controlled in accordance with the position of the defects in the multilayer reflective film 31. Subsequently, the unnecessary parts of the absorber layer 34 and the low-reflection layer 35, and the resist are removed by development and etching to give the reflective photomask 100.

The reflective photomask 100 has the low-reflection layer 135 and the absorber layer 134 given by patterning the low-reflection layer 35 and the absorber layer 34 shown in FIG. 1. The EUV light radiated to the reflective photomask 100 is absorbed in the area having the absorber layer 134 but is reflected by the multilayer reflective film 31 in the area not having the absorber layer 134, therefore forming an image on the surface of the exposed material by an optical system or the like. In that manner, the pattern of the absorber layer 134 is transferred to the surface of the exposed material.

(Substrate)

The substrate 20 is one for forming the multilayer reflective film 31 and others thereon. RMS (Root Mean Square) that indicates the surface roughness of the substrate 20 is, for example, at most 0.15 nm, and the degree of flatness of the substrate 20 is, for example, at most 100 nm. The thermal expansion coefficient of the substrate 20 is, for example, $0\pm0.05\times10^{-7}/°C$., preferably $0\pm0.03\times10^{-7}/°C$.

Preferably, the substrate 20 is formed of glass excellent in chemical resistance and heat resistance and having a small thermal expansion coefficient. As the glass, for example, usable here is quartz glass containing $SiO_2$ as the main ingredient thereof. The quartz glass may contain $TiO_2$. The content of $TiO_2$ is, for example, from 1 to 12% by mass. The substrate 20 may also be formed of silicon, metal or the like except glass.

A conductive layer 22 for electrostatic adsorption is formed on the back surface 21 of the substrate 20. For the conductive layer 22, the electric conductivity and the thickness of the constituent material thereof are selected so that the sheet resistance of the layer could be at most 100 Ω/square. As the constituent material of the conductive layer 22, for example, usable here are Si, TiN, Mo, Cr, CrN, CrO, TaSi, etc. Of those, preferred is a CrN film, because the surface roughness of the surface of the conductive layer 22 is small and therefore the layer is excellent in adhesion to a chuck face and because the sheet resistance of the conductive layer 22 is low and therefore the layer is excellent in chuck force.

The thickness of the conductive layer 22 is, for example, from 10 to 1000 nm.

As the method for forming the conductive layer 22, it can be used a known film formation method, for example, a sputtering method such as a magnetron sputtering method or an ion beam sputtering method, as well as a CVD method, a vacuum evaporation method, an electrolytic plating method, etc.

The multilayer reflective film 31 and others are formed on the surface 23 of the substrate 20.

(Multilayer Reflective Film)

The multilayer reflective film 31 reflects EUV light. The EUV light radiated to the area not having the absorber layer 134 in the reflective photomask 100 is reflected by the multilayer reflective film 31. The maximum value of the reflectivity (light reflectivity at a wavelength of 13.5 nm or so) is, for example, at least 60% and is preferably at least 63%.

The multilayer reflective film 31 is formed by repeatedly stacking multiple kinds of layers each having a different refractive index in a prescribed order. For example, the multilayer reflective film 31 is a Mo/Si multilayer reflective film formed by alternately and repeatedly stacking Mo layers as low refraction layers and Si layers as high refraction layers. The thickness of the Mo layer, the thickness of the Si layer and the number of pairs of the Mo layer and the Si layer may be suitably defined; and for example, the thickness of the Mo layer is 2.3±0.1 nm, the thickness of the Si layer is 4.5±0.1 nm, and the number of pairs of the Mo layer and the Si layer is from 30 to 60. The thickness of the multilayer reflective film 31 is, for example, from 200 to 400 nm.

Not specifically limited, the multilayer reflective film 31 may be, for example, a Ru/Si multilayer reflective film, a Mo/Be multilayer reflective film, a Mo compound/Si compound multilayer reflective film, a Si/Mo/Ru multilayer reflective film, a Si/Mo/Ru/Mo multilayer reflective film, a Si/Ru/Mo/Ru multilayer reflective film, etc.

As the method for film formation of the multilayer reflective film 31, it can be used a film formation method such as a magnetron sputtering method, an ion beam sputtering method, etc. Film formation of a Mo/Si multilayer reflective film according to an ion beam sputtering method contains alternate repetition of a step of forming a Mo layer with a Mo target and a step of forming a Si layer with a Si target.

(Protective Layer)

The protective layer 32 prevents oxidation of the multilayer reflective film 31. As the material of the protective layer 32, it can be used Si, Ti, Ru, Rh, C, SiC, as well as mixtures of these elements/compounds, and those prepared by adding N, O, B or the like to these elements/compounds.

Using a Ru or a Ru compound as the material for the protective layer 32 is especially preferred, since the layer thickness can be made thin such as from 1 to 5 nm, and since the layer can additionally have the function of the buffer layer 33 to be mentioned below. In cases where the multilayer reflective film 31 is a Mo/Si multilayer reflective film and where the uppermost layer therein is a Si layer, the uppermost layer can function as the protective layer. In this case, the thickness of the Si layer of the uppermost layer is preferably from 5 to 15 nm, which is larger than ordinary 4.5 nm. Also in this case, a Ru film or a Ru compound film that serves both as the protective layer 32 and as the buffer layer 33 can be formed on the uppermost Si layer. The protective layer 32 is not always needed to be one layer alone but may contain 2 or more layers.

For film formation for the protective layer 32, it can be used a film formation method such as a magnetron sputtering method, an ion beam sputtering method, etc.

(Buffer Layer)

The buffer layer 33 prevents the multilayer reflective film 31 from being damaged in the etching process (generally dry etching process) for the absorber layer 34 during the production process for the reflective photomask 100.

As the material for the buffer layer 33, herein selected is a substance that is hardly influenced by the etching process for the absorber layer 34, that is, a substance of which the etching rate is lower than that of the absorber layer 34 and which is hardly damaged by the etching process. Examples of the substance satisfying these requirements include Cr, Al, Ru, Ta and nitrides thereof, as well as $SiO_2$, $Si_3N_4$, $Al_2O_3$ and mixtures thereof. Of those, preferred are Ru, Ru compounds, CrN and $SiO_2$; more preferred are CrN, Ru and Ru compounds; and especially preferred are Ru and Ru compounds for satisfying both the functions of the protective layer 32 and the buffer layer 33.

Preferably, the thickness of the buffer layer 33 is from 1 to 60 nm.

As the film formation method for the buffer layer 33, it can be used any known film formation method such as a magnetron sputtering method, an ion beam sputtering method, etc.

(Absorption Layer)

The absorber layer 34 is a layer that absorbs EUV light. The characteristic especially required for the absorber layer 34 is to control the intensity and the phase of the reflected light from the absorber layer 34 in order that the pattern formed in the reflective photomask 100 could be accurately transferred to the resist film on a wafer via a projection optical system of an EUV exposure apparatus.

There are two concrete methods for the above. The first is a method of minimizing the intensity of the reflected light from the absorber layer 34, for which the thickness and the material of the absorber layer 34 are controlled so that the EUV light reflectivity from the surface of the absorber layer 34 (in cases where a low-reflection layer is formed on the surface of the absorber layer, from that low-reflection layer) could be at most 1%, and especially at most 0.7%. The second is a method of utilizing the interference effect of the reflected light from the multilayer reflective film 31 and the reflective light from the surface of the absorber layer 34 (in cases where a low-reflection layer is formed on the surface of the absorber layer, from that low-reflection layer), for which the thickness and the material of the absorber layer 34 are controlled so that the EUV light reflectivity from the absorber layer 34 (in cases where a low-reflection layer is formed on the surface of the absorber layer, from that low-reflection layer) could be at most 15% (e.g., from 2 to 15%) and that the phase difference between the reflected light from the multilayer reflective film 31 and the reflected light from the absorber layer 34 (in cases where a low-reflection layer is formed on the surface of the absorber layer, from that low-reflection layer) could be from 175 to 185 degrees. In the first method, the thickness of the absorber layer 34 is preferably at least 60 nm, and more preferably at least 70 nm. In the second method, the thickness is preferably within a range of from 20 nm to 60 nm, and more preferably within a range of from 25 nm to 55 nm.

In any method, preferably, the material to constitute the absorber layer 34 is a material that contains Ta in an amount of at least 40 at %, more preferably at least 50 at %, and even more preferably at least 55 at %. The material that contains Ta as the main ingredient thereof for use for the absorber layer 34 preferably contains at least one or more elements of Hf, Si, Zr, Ge, B, Pd, Pt, H and N, in addition to Ta.

Specific examples of the material containing the above element in addition to Ta include TaN, TaNH, TaHf, TaHfN, TaBSi, TaBSiN, TaB, TaBN, TaSi, TaSiN, TaGe, TaGeN, TaZr, TaZrN, TaPd, TaPdN, TaPt, TaPtN, etc. However, it is desirable that the absorber layer 34 does not contain oxygen.

Concretely, it is desirable that the oxygen content in the absorber layer 34 is less than 25 at %. In producing the reflective photomask 100 for EUV by forming a mask pattern in the absorber layer 34 of the reflective mask blank 10, generally employed is a dry etching process, in which chlorine gas (including mixed gas) or fluorine gas (including mixed gas) is generally used as the etching gas.

In cases where a Ru layer or a Ru compound layer, which serves as both the protective layer 32 and the buffer layer 33, is formed on the multilayer reflective film 31 for the purpose of preventing the multilayer reflective film 31 from being damaged in the etching process, chlorine gas is mainly used as the etching gas for the absorber layer 34 as giving little damage to the Ru layer or the Ru compound layer. However, in the dry etching process where chlorine gas is used for etching the absorber layer 34, when the absorber layer 34 contains oxygen, then it is unfavorable since the etching rate would lower and the resist film may be seriously damaged. Consequently, the oxygen content in the absorber layer 34 is more preferably at most 15 at %, even more preferably at most 10 at %, and especially preferably at most 5 at %.

As the method for forming the absorber layer 34, it can be used a film formation method such as a magnetron sputtering method, an ion beam sputtering method, etc.

In the process for producing the reflective photomask 100, the absorber layer 34 is patterned in a prescribed manner to be the absorber layer 134.

(Low-Reflection Layer)

The low-reflection layer 35 is a layer having a lower reflectivity than the absorber layer 34 with respect to the inspection light for inspecting the pattern of the absorber layer 134. As the inspection light, for example, it can be used a light having a wavelength of around 257 nm or around 193 nm.

The pattern profile of the absorber layer 134 is inspected by utilizing the difference in the reflectivity with respect to the inspection light between the part where the absorber layer 134 exists and the part where the absorber layer 134 is absent. In the part where the absorber layer 134 is absent, in general, the buffer layer 33 (or the protective layer 32 when the buffer layer 33 is absent) is exposed out.

In cases where the low-reflection layer 135 is stacked in the part where the absorber layer 134 exists, the difference in the reflectivity to the inspection light increases between the part where the absorber layer 134 exists and the part where the absorber layer 134 is absent, and in the case, therefore, the inspection accuracy improves.

The low-reflection layer 35 is formed of a material of which the reflectivity at the wavelength of the inspection light is lower than that of the absorber layer 34. Concretely, there is mentioned a material containing Ta as the main ingredient thereof. The material contains at least one or more element of Hf, Ge, Si, B, N, H and O, in addition to Ta.

Specific examples thereof include TaO, TaON, TaONH, TaBO, TaHfO, TaHfON, TaBSiO, TaBSiON, SiN, SiON, etc.

In cases where the low-reflection layer 35 is formed on the absorber layer 34, the total thickness of the absorber layer 34 and the low-reflection layer 35 is preferably from 10 to 65 nm, more preferably from 30 to 65 nm, and even more preferably from 35 to 60 nm. When the thickness of the low-reflection layer 35 is larger than the thickness of the absorber layer 34, then the EUV absorption characteristic of the absorber layer 34 may worsen; and therefore, it is desirable that the thickness of the low-reflection layer 35 is smaller than the thickness of the absorber layer 34. Consequently, the thickness of the low-reflection layer 35 is preferably from 1 to 20 nm, more preferably from 3 to 15 nm, and even more preferably from 5 to 10 nm.

As the method for forming the low-reflection layer 35, it can be used a film formation method such as a magnetron sputtering method, an ion beam sputtering method, etc. Using EUV light as the inspection light is under investigation; and in cases where EUV light is used for inspection, the low-reflection layer may not be formed.

(Other Functional Layers)

Other functional layers include, for example, a hard mask. The hard mask is formed on the surface of the absorber layer 34 (or the low-reflection layer 35 in cases where the low-reflection layer 35 is formed on the absorber layer 34 and where the low-reflection layer 35 does not have the function of a hard mask). Since the above-mentioned dry etching rate for the hard mask is low as compared with that for the absorber layer 34 and/or the low-reflection layer 35, the thickness of the resist film may be reduced and a finer micropattern can be therefore formed. As the material for the hard mask, it can be used CrN, CrO, CrON, Ru, etc. The thickness thereof is preferably from 2 to 10 nm.

(Temporary Fiducial Mark)

Figure 3:
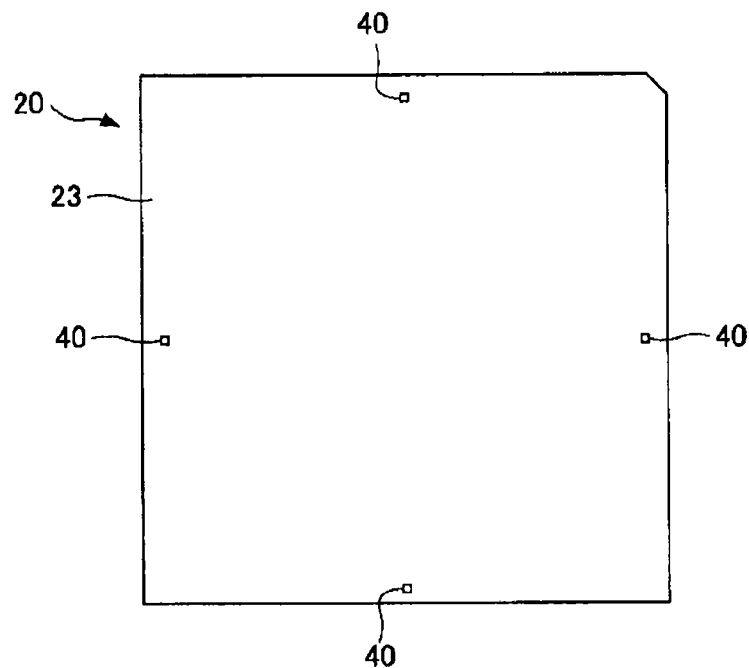
FIG. 3 is a plan view of one example of a substrate and a temporary fiducial mark formed on a surface of the substrate.

FIG. 3 is a plan view of one example of a substrate and a temporary fiducial mark formed on a surface of the substrate.

The temporary fiducial mark 40 is a mark that indicates a reference position of the substrate 20. The temporary fiducial mark 40 is formed in the surface 23 of the substrate 20. Before the formation of the multilayer reflective film 31, the position of the defect of the substrate 20 can be identified based on the position of the temporary fiducial mark 40 as the reference position, and can be recorded on a recording medium. As the recording medium, it can be used a magnetic recording medium, an optical recording medium, an electronic recording medium, paper, etc.

At least three (in FIG. 3, four) temporary fiducial marks 40 are formed on the surface 23 of the substrate 20. These temporary fiducial marks 40 are not arranged on one and the same line. Of the reference points (e.g., the center points) indicated by those temporary fiducial marks 40, one reference point is taken as the origin; and the line that connects the origin to another one reference point is the X axis, while the line that connects the origin to the remaining one reference point is the Y axis. The X axis and the Y axis may be perpendicular to each other. Using this XY coordinate system, the position of the defect can be identified.

The temporary fiducial mark 40 is formed in the region not used in the later process (e.g., in the region not to be patterned in the production process for the reflective photomask), and concretely, it is desirable that the mark is formed in the outer peripheral region of the substrate 20.

The temporary fiducial mark 40 is formed in a concave shape or in a convex shape (in this embodiment, concave shape) on the surface 23 of the substrate 20. The convex-shaped temporary fiducial mark will be described in the second embodiment.

The concave-shaped temporary fiducial mark 40 is formed by removing a part of the surface 23 of the substrate 20. As the removing method, it can be used a laser ablation method, an FIB method, a nanoindentation method, a micromachining method (e.g., a mechanical micromachining method using nm450 manufactured by Rave), a lithography method that uses resist patterning and etching, etc. Especially preferred are an FIB method, a micromachining method, and a laser ablation method.

As the concave-shaped temporary fiducial mark 40, it can also be used a real defect existing in the surface 23 of the substrate 20, for example, a concave-shaped defect such as a pit or the like formed during polishing or washing and existing therein.

On the planar view thereof (seen in the direction perpendicular to the surface 23 of the substrate 20), the shape of the concave-shaped temporary fiducial mark 40 may be, for example, a square as shown in FIG. 3, triangular, circular, oval, rhombic or the like one; while on the side view thereof, the shape may be, for example, a triangular as shown in FIG. 1, square, semi-circular or the like one.

Regarding the size of the concave-shaped temporary fiducial mark 40, for example, on the planar view thereof, the maximum length is at most 200 nm, preferably at most 70 nm and more preferably at most 50 nm, and the minimum length is at least 10 nm and preferably at least 30 nm. The maximum depth of the concave-shaped temporary fiducial mark 40 is at most 20 nm, preferably at most 10 nm and more preferably at most 5 nm. The minimum depth of the concave-shaped temporary fiducial mark 40 is at least 1 nm and preferably at least 2 nm. The temporary fiducial mark 40 having a size that falls within the range can secure the detection sensitivity with a commercial automatic defect inspection apparatus (e.g., M7360 manufactured by Lasertec) for reflective mask blanks and glass substrates, which uses UV light or visible light as the light source, and in addition, since the detection spot is not so large as to worsen the detection position reproducibility, the detection position reproducibility can be kept good. Consequently, the position of the defect existing in the surface 23 of the substrate 20 can be identified with sufficient accuracy.

The concave-shaped temporary fiducial mark 40 is transferred to the layer formed on the temporary fiducial mark 40. For example, the temporary fiducial mark 40 is transferred to the multilayer reflective film 31, the protective layer 32, the buffer layer 33, the absorber layer 34 and the low-reflection layer 35, as shown in FIG. 1.

The temporary fiducial mark 40 of the surface of the substrate 20 may be omitted. In a case of using a current optical defect inspection apparatus, the inspection sensitivity on the multilayer reflective film 31 is higher than on the substrate 20, and accordingly, the defect of the substrate 20 can be transferred to the multilayer reflective film 31 and can be therefore detected on the multilayer reflective film 31. In cases where a defect (e.g., foreign substance, flaw, pit) exists in the surface of the substrate on which the multilayer reflective film 31 is formed, the periodical structure of the multilayer reflective film 31 may be disordered and defects (so-called phase defects) would be thereby formed in the multilayer reflective film.

(Fiducial Mark)

The fiducial mark 50 is a mark that indicates a reference position of the multilayer reflective film 31. The fiducial mark 50 is formed in a concave shape or in a convex shape (in this embodiment, concave shape) on the surface of the multilayer reflective film 31 or on the surface of the layer 32 or 33 formed between the multilayer reflective film 31 and the absorber layer 34 (in this embodiment, on the buffer layer 33). Before the formation of the absorber layer 34, the position of the defect of the multilayer reflective film 31 can be identified, based on the position of the fiducial mark 50 as a reference position, and can be recorded on a recording medium.

Though the details are described below, in cases where the fiducial mark 50 is formed on the surface of the buffer layer 33 (or on the surface of the protective layer 32), the position of the defect of the multilayer reflective film 31 can be identified collectively along with the position of the defect of the buffer layer 33 (or the position of the defect of the protective layer 32).

The fiducial mark 50 is transferred to the layer (e.g., the absorber layer 34, the low-reflection layer 35) formed on the fiducial mark 50 to be a mark (Fiducial Mark) that indicates the reference position for the reflective mask blank 10. The transferred fiducial mark has nearly the same dimension and shape as those of the originally-formed fiducial mark 50. The position of the transferred fiducial mark is detected, and with reference to the information recorded on the recording medium, the position of the defect in the multilayer reflective film 31 can be thereby known.

Figure 4:
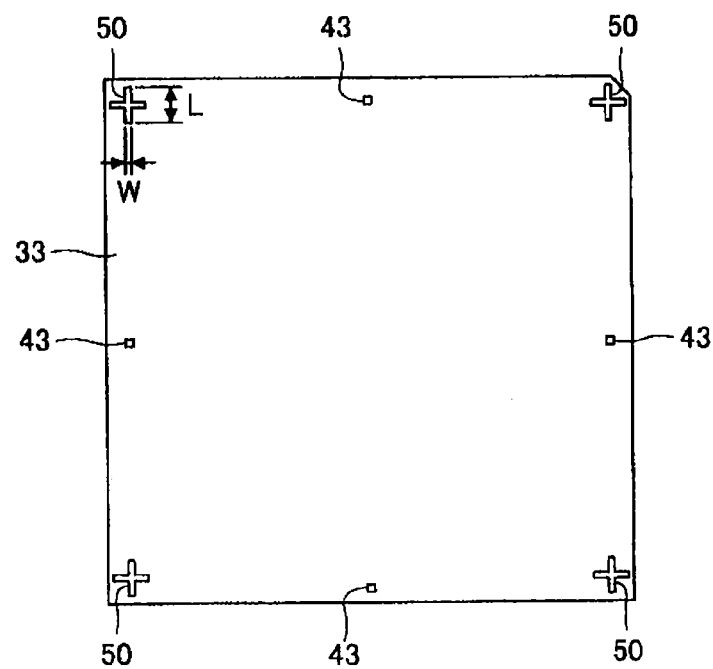
FIG. 4 is a plan view of one example of a fiducial mark formed on a surface of the layer formed between a multilayer reflective film and an absorber layer.

FIG. 4 is a plan view of one example of the fiducial mark formed on the surface of the buffer layer 33 formed between the multilayer reflective film 31 and the absorber layer 34. The fiducial mark 50 shown in FIG. 4 and FIG. 1 is formed on the surface of the buffer layer 33, but may be formed on the surface of the protective layer 32 or on the surface of the multilayer reflective film 31.

The fiducial mark 50 may be formed to have any desired shape depending on the intended use thereof. For example, the fiducial mark 50 is formed as a cross on the planar view thereof (seen in the direction perpendicular to the surface on which the fiducial mark 50 is formed), as shown in FIG. 4. The point of intersection between the centerline in one linear part and the centerline in the other linear part is the reference point.

Preferably, the fiducial mark 50 has a size detectable in observation at a low magnification, and the size thereof may be defined in accordance with the dimensional tolerance and the like of the reflective mask blank 10. The dimensional tolerance of one side (152.0 mm) of a standard square reflective mask blank is ±0.1 mm. When the reflective mask blank is set in a prescribed apparatus (e.g., in an electron beam image-drawing apparatus), for example, the two sides of the reflective mask blank are pressed against pins for positioning. In this stage, the position of the fiducial mark 50 could move by ±0.1 mm in every reflective mask blank. Therefore, for detecting the position within a short period of time, it is desirable that the fiducial mark 50 has a size detectable in observation at a low magnification. In cases where the dimensional tolerance is ±0.1 mm, it is desirable that the area of the fiducial mark 50 on the planar view thereof is from 1 $\mu m^2$ to 1 $mm^2$. Each linear part of the cruciform fiducial mark 50 may be, for example, such that the width W thereof is from 0.2 to 10 $\mu m$ and the length L thereof is from 10 to 500 $\mu m$. In this case, the area of the fiducial mark 50 on the planar view thereof is from 3.96 $\mu m^2$ to 9900 $\mu m^2$.

At least three fiducial marks 50 are formed on the surface for forming the fiducial marks thereon (in this embodiment, on the surface of the buffer layer 33). These at least three fiducial marks 50 are not arranged on one and the same line. Of these at least three reference points, one reference point is taken as the origin; and the line that connects the origin to another reference point is the X axis, while the line that connects the origin to the remaining one reference point is the Y axis. The X axis and the Y axis may be perpendicular to each other. Using this XY coordinate system, the position of the defect can be identified.

The fiducial mark 50 is formed in the region not used in the later process in the multilayer reflective film 31 (e.g., in the region not to be patterned in the production process for the reflective photomask), and concretely, the mark is formed in the outer peripheral region of the surface on which the fiducial mark 50 is formed.

On the planar view thereof, the fiducial mark 50 may be formed in the position separated from the temporary fiducial mark 40. On the planar view thereof, the fiducial mark 50 may be formed in the position where it overlaps with the temporary fiducial mark 40, and this will be described in the fifth embodiment.

The fiducial mark 50 is formed, for example, in a concave shape in the surface of the multilayer reflective film 31, the protective layer 32 or the buffer layer 33 (that is, in the surface opposite to the side of the substrate 20). The convex-shaped fiducial mark 50 is described in the second embodiment.

The concave-shaped fiducial mark 50 is formed by removing a part of the multilayer reflective film 31. The concave-shaped fiducial mark 50 may also be formed by removing a part of the buffer layer 33 and a part of the protective layer 32 to run through the buffer layer 33 and the protective layer 32 after the formation of the buffer layer 33, for example, as shown in FIG. 1.

As the removing method, it can be used a laser ablation method, an FIB (Focused Ion Beam) method, a lithography method that uses resist patterning and etching, a nanoindentation method, a micromachining method (e.g., a mechanical micromachining method using nm450 manufactured by Rave), etc. Of these, in a laser ablation method and an FIB method, the material of the bottom of the fiducial mark 50 may be denatured by the laser light or the metal ions used for the processing. For example, the bottom of the fiducial mark 50 may be oxidized or nitrided. In a case of a Mo/Si multilayer reflective film, the bottom of the fiducial mark 50 may be converted into a MoSi compound. In that manner, since the material of the bottom of the fiducial mark 50 may denature, the contrast between the bottom of the fiducial mark 50 and the peripheral part of the fiducial mark 50 may increase. In particular, an FIB method is preferred as enabling fine micromachining.

Preferably, the concave-shaped fiducial mark 50 has a step face 50a that is nearly perpendicular to the face of forming the fiducial mark 50 and an offset face (inner bottom face) 50b that is nearly parallel to the face of forming the fiducial mark 50, in order that the edges of the mark can be sharp, as shown in FIG. 1.

The concave-shaped fiducial mark 50 is formed after the formation of the multilayer reflective film 31, and therefore the edges thereof are sharp and the side wall angles thereof are steep, as compared with those of the temporary fiducial mark 43 transferred on the face on which the fiducial mark 50 is formed.

In addition, the concave-shaped fiducial mark 50 differs from the peripheral area around the fiducial mark 50 in point of the reflectivity thereof to light having a prescribed wavelength (inspection light for the multilayer reflective film 31). As the inspection light, it can be used EUV light, far-UV light, visible light, etc. Of those, EUV light can reach the inside of the multilayer reflective film 31, therefore enabling inside inspection.

The concave-shaped fiducial mark 50 in this embodiment is formed by removing a part of the multilayer reflective film 31, and therefore the reflectivity thereof to inspection light of EUV light is low as compared with that of the multilayer reflective film 31 in the area around the fiducial mark 50. As a result, the contrast between the fiducial mark 50 and the area around it increases, and the reproducibility of the detection position of the fiducial mark 50 is thereby bettered. Consequently, based on the position of the fiducial mark 50 as a reference position, the position of the defect in the multilayer reflective film 31 can be accurately identified. The difference (absolute difference) between the reflectivity to the inspection light of the fiducial mark 50 and the reflectivity to the inspection light in the area around the fiducial mark 50 is preferably at least 0.2%, more preferably at least 0.5% and even more preferably at least 1.0%.

Figure 5:
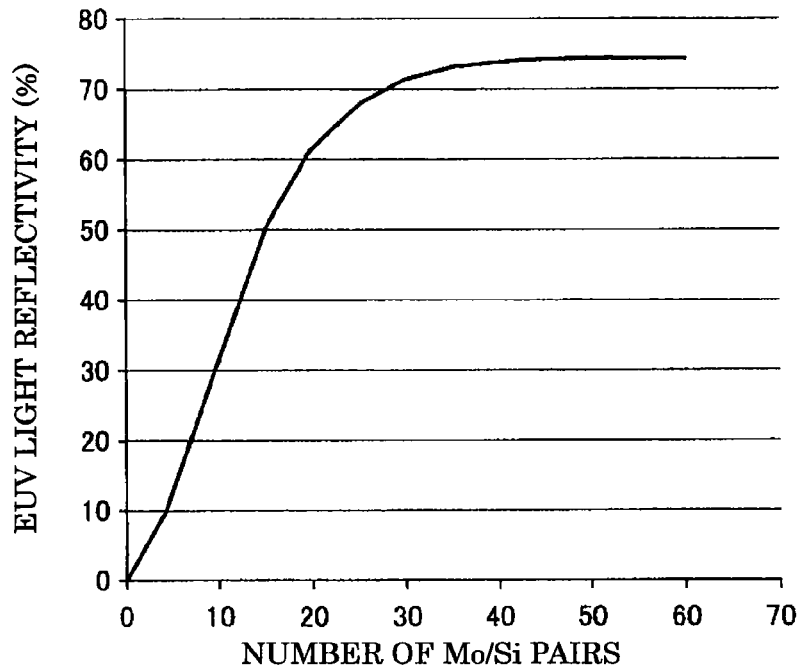
FIG. 5 is a view showing the relationship between EUV light reflectivity of a Mo/Si multilayer reflective film and the number of Mo/Si pairs in the film.

FIG. 5 is a view showing the relationship between the EUV light reflectivity of a Mo/Si multilayer reflective film and the number of Mo/Si pairs in the film. In FIG. 5, the thickness of the Mo layer is 2.3±0.1 nm, the thickness of the Si layer is 4.5±0.1 nm, and the wavelength of the EUV light is 13.5 nm. As shown in FIG. 5, the EUV light reflectivity lowers with the decrease in the number of the pairs of the Mo layer and the Si layer.

For increasing the EUV light reflectivity during photoexposure, it is desirable that the pair number is at least 30 and more preferably at least 35. On the other hand, with the increase in the pair number, the film stress increases and the degree of flatness of the reflective photomask lowers. Accordingly, the pair number is preferably at most 60, more preferably at most 55 and even more preferably at most 50.

Next described is a method for forming the fiducial mark 50 in the case of inspecting the Mo/Si multilayer reflective film with EUV light, with reference to FIG. 5.

In cases where the face for forming thereon the fiducial mark 50 is the surface of the Mo/Si multilayer reflective film, it is desirable that the fiducial mark 50 is formed by removing at least two pairs of Mo layer/Si layer and more preferably at least five pairs thereof for increasing the contrast to the peripheral area. Since the thickness of the pair of Mo layer/Si layer is about 7 nm, the depth of the fiducial mark 50 could be at least about 14 nm in the former and could be at least about 35 nm in the latter. In this case, the EUV light reflectivity of the fiducial mark 50 is low as compared with that in the area around the mark.

In cases where the face for forming thereon the fiducial mark 50 is the surface of the protective layer 32 (or the buffer layer 33), it is desirable that the fiducial mark 50 is formed to run through the protective layer 32 (or both of the protective layer 32 and the buffer layer 33) further by removing at least two pairs of Mo layer/Si layer and more preferably at least five pairs thereof for increasing the contrast to the peripheral area. In this case, the EUV light reflectivity of the fiducial mark 50 is low as compared with that in the area around the mark.

Irrespective of the type of the face for forming thereon the fiducial mark 50, the material of the bottom of the fiducial mark 50 may be the MoSi compound to be formed by reaction of the Mo layer and the Si layer in processing the fiducial mark 50. The EUV light reflection results from the difference in the refraction between the Mo layer and the Si layer. Formation of the MoSi compound by reacting the Mo layer and the Si layer cancels the refraction difference, and the EUV light reflectivity of the fiducial mark 50 can be thereby further lowered.

Figure 6:
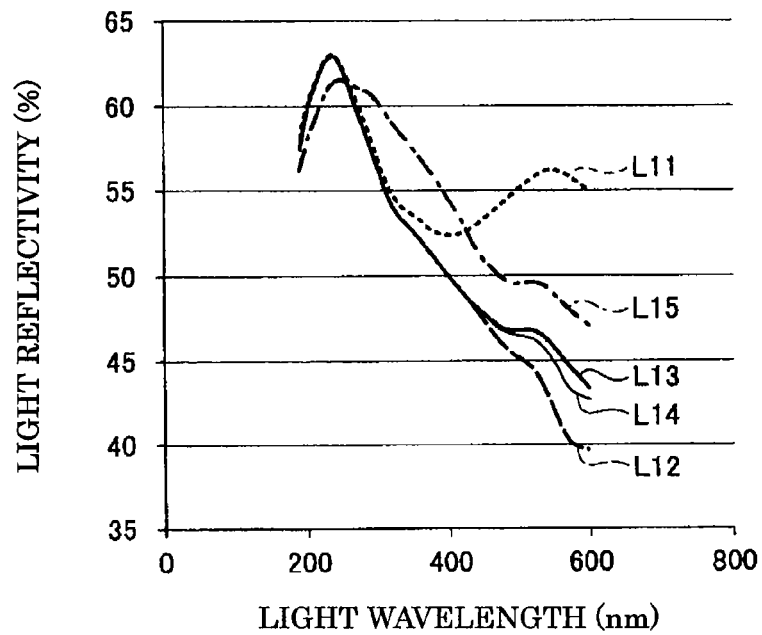
FIG. 6 is a view showing the relationship between light reflectivity of a Mo/Si multilayer reflective film and a light wavelength.
Figure 7:
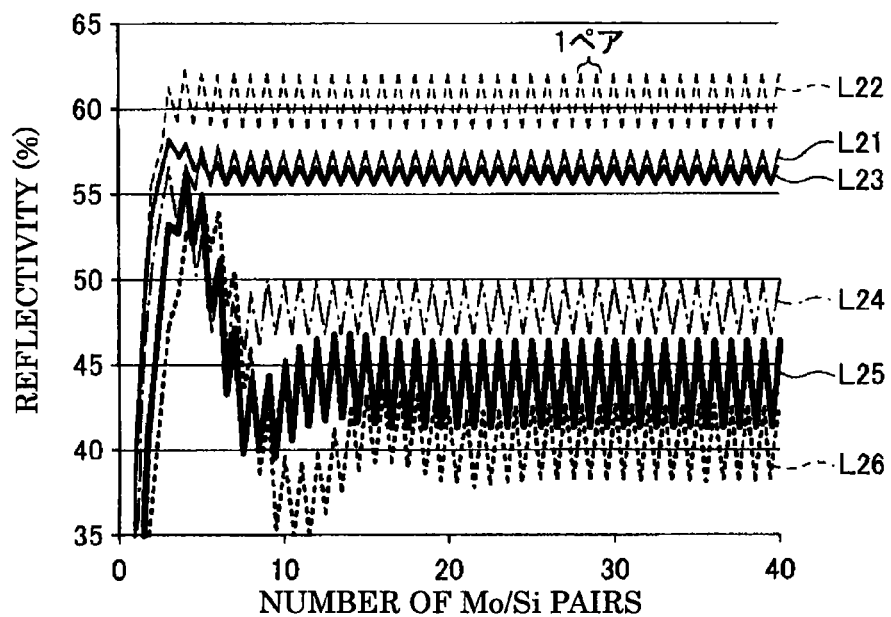
FIG. 7 is a view showing the relationship between light reflectivity of a Mo/Si multilayer reflective film and the number of Mo/Si pairs in the film.

Next described is a method for forming the fiducial mark 50 in a case of inspecting the Mo/Si multilayer reflective film with far-UV light or visible light, with reference to FIG. 7 and FIG. 6.

FIG. 7 is a view showing the relationship between the light reflectivity of the Mo/Si multilayer reflective film and the number of Mo/Si pairs in the film. In FIG. 7, the thickness of the Mo layer is 2.3±0.1 nm, and the thickness of the Si layer is 4.5±0.1 nm. In FIG. 7, the line L 21 indicates the relationship in which the light wavelength is 190 nm; the line L 22 indicates the relationship in which the light wavelength is 257 nm; the line L 23 indicates the relationship in which the light wavelength is 300 nm; the line L 24 indicates the relationship in which the light wavelength is 400 nm; the line L 25 indicates the relationship in which the light wavelength is 500 nm; and the line L 26 indicates the relationship in which the light wavelength is 600 nm. Different from FIG. 5 and FIG. 6, FIG. 7 shows the light reflectivity of every one layer (0.5 pairs), in addition to the light reflectivity of every one pair.

As shown in FIG. 7, in cases where the pair number is 10 or more, the far-UV or visible light reflectivity varies mainly depending on the surface material on the light-incident side of the Mo/Si multilayer reflective film. Accordingly, in a case where the face for forming thereon the fiducial mark 50 is the surface of the Mo/Si multilayer reflective film, it is desirable that the material of the bottom of the fiducial mark 50 differs from the material of the uppermost layer (the layer on the side opposite to the substrate side) of the Mo/Si multilayer reflective film, for increasing the contrast to the peripheral area. For example, in a case where the uppermost layer of the multilayer reflective film is Si, the material of the bottom of the fiducial mark 50 may be the MoSi compound to be formed by reacting the Mo layer and he Si layer in processing the fiducial mark 50. In this case, the far-UV reflectivity and the visible light reflectivity of the fiducial mark 50 are lower than those in the area around the mark. In addition, the material of the bottom of the fiducial mark 50 may also be an oxide, a nitride or an oxynitride of Mo, Si or MoSi compound to be formed by oxidation, nitridation or oxynitridation of the Mo layer or the Si layer in processing the fiducial mark 50. In this case, the far-UV reflectivity and the visible light reflectivity of the fiducial mark 50 are lower than those in the area around the mark.

As shown in FIG. 7, when the pair number is at most 5, the reflectivity to visible light (L24 to L26) increases, and therefore the fiducial mark 50 with the pair number of at most 5 may be formed. In this case, the visible light reflectivity of the fiducial mark 50 is higher than that in the area around the mark.

FIG. 6 is a view showing the relationship between the light reflectivity of the Mo/Si multilayer reflective film and the light wavelength. In FIG. 6, the thickness of the Mo layer is 2.3±0.1 nm, and the thickness of the Si layer is 4.5±0.1 nm. In FIG. 6, the line L 11 indicates the relationship in which the pair number is 5; the line L 12 indicates the relationship in which the pair number is 10; the line L 13 indicates the relationship in which the pair number is 15; the line L 14 indicates the relationship in which the pair number is 40; and the line L 15 indicates the relationship in which an additional Ru layer is further formed on the Mo/Si multilayer reflective film having a pair number of 40. The Ru layer serves both as a protective layer and a buffer layer and the thickness of the Ru layer is 2.5 nm.

As shown in FIG. 6, the far-UV reflectivity and the visible light reflectivity vary depending on the presence or absence of the Ru layer. Consequently, in cases where the fiducial mark 50 is formed on the surface of the Ru layer, it is desirable that the fiducial mark 50 to be formed has a concave shape that runs through the Ru layer, for the purpose of increasing the contrast between the fiducial mark 50 and the area around the mark. The material of the bottom of the fiducial mark 50 differs from the material of the Ru layer. In this case, the light reflectivity of the fiducial mark 50 could be higher or lower than that in the area around the mark.

The fiducial mark 50 is formed after the formation of the multilayer reflective film 31, and is transferred to the absorber layer 34 or the like that is thinner (about ¼ or so) than the multilayer reflective film 31. Accordingly, the transferred fiducial mark 55 is to have nearly the same shape as that of the original fiducial mark 50, therefore bettering the reproducibility of the detection position with the inspection light (electron beam, far-UV light, visible light, EUV light) and providing the following advantageous effects (1) and (2). (1) In the process for producing the reflective photomask 100, an electron beam image-drawing apparatus (e.g., EBM8000 manufactured by Nuflare, etc.), a laser image-drawing apparatus, a mask pattern coordinate measuring apparatus (e.g., IPRO5 manufactured by KLA-Tencor, etc.) or a mask pattern inspection apparatus (e.g., Teron 610 manufactured by KLA-Tencor, etc.) can detect the position of the fiducial mark 55 with electron beam or far-UV light at good reproducibility. Accordingly, these apparatuses enable good and accurate detection of the position of the defect in the multilayer reflective film 31 and the like, based on the information provided by the supplier of the reflective mask blank 10. (2) In inspection of the absorber layer 34 and the low-reflection layer 35, the position of the fiducial mark 55 can be detected at good producibility with far-UV light or visible light.

Figure 8:
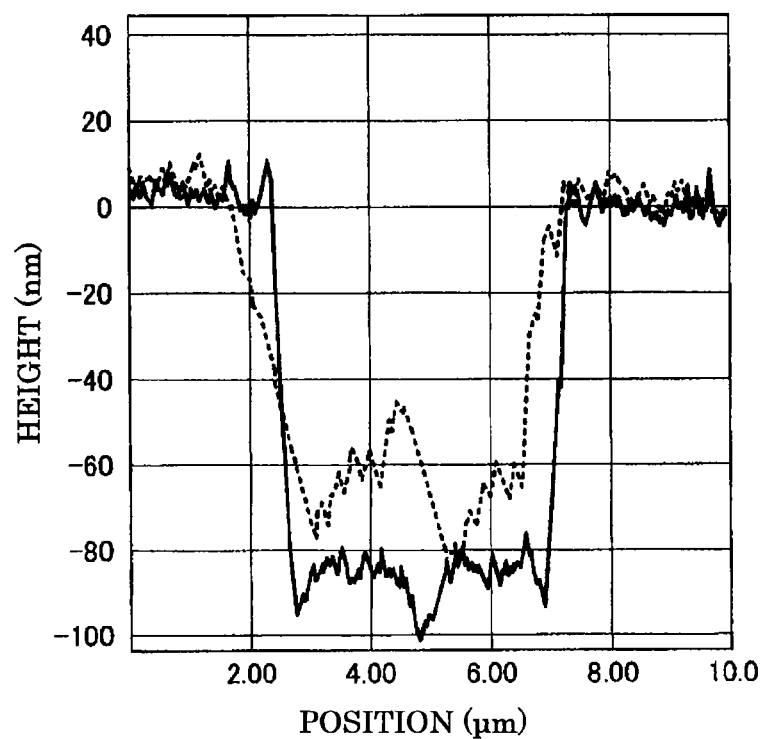
FIG. 8 is a comparative view showing the cross-sectional profiles of the fiducial mark transferred on a reflective mask blank in an example of the present invention and in a conventional example.

FIG. 8 is a comparative view showing the cross-sectional profile of the fiducial mark transferred on the reflective mask blank in an example of the present invention and in a conventional example. In FIG. 8, the full line indicates the cross-sectional profile in an example of the present invention; and the dotted line indicates the cross-sectional profile in a conventional example. The reflective mask blank used contains, as formed on a TiO$_2$-doped quartz glass substrate in the listed order, a Mo/Si multilayer reflective film as the multilayer reflective film, a Ru layer as the protective layer and the buffer layer, a TaN layer as the absorber layer, and a TaON layer as the low-reflection layer. In the reflective mask blank, the fiducial mark in the example of the present invention is formed as a concave shape (depth 80 nm) in the Ru layer by removing a part of the Ru layer (thickness 2.5 nm) and a part of the Mo/Si multilayer reflective film (thickness 280 nm), and is transferred to the TaN layer (thickness 51 nm) and the TaON layer (thickness 7 nm). On the other hand, the fiducial mark in the conventional example is formed as a concave shape (depth 80 nm) in the substrate and is transferred to the Mo/Si multilayer reflective film (thickness 280 nm), the Ru layer (thickness 2.5 nm), the TaN layer (thickness 51 nm) and the TaON layer (thickness 7 nm).

As shown in FIG. 8, the fiducial mark in the example of the present invention gives a steeper cross-sectional profile when transferred to the reflective mask blank, as compared with the fiducial mark in the conventional example.

Second Embodiment

In the above first embodiment, the temporary fiducial mark and the fiducial mark are formed in concave shape. As opposed to the case, in this embodiment, the temporary fiducial mark and the fiducial mark are formed in convex shape. This embodiment is the same as the first embodiment except for the difference in the shape of the temporary fiducial mark and in the shape of the fiducial mark, and is therefore described here mainly in point of the difference.

Figure 9:
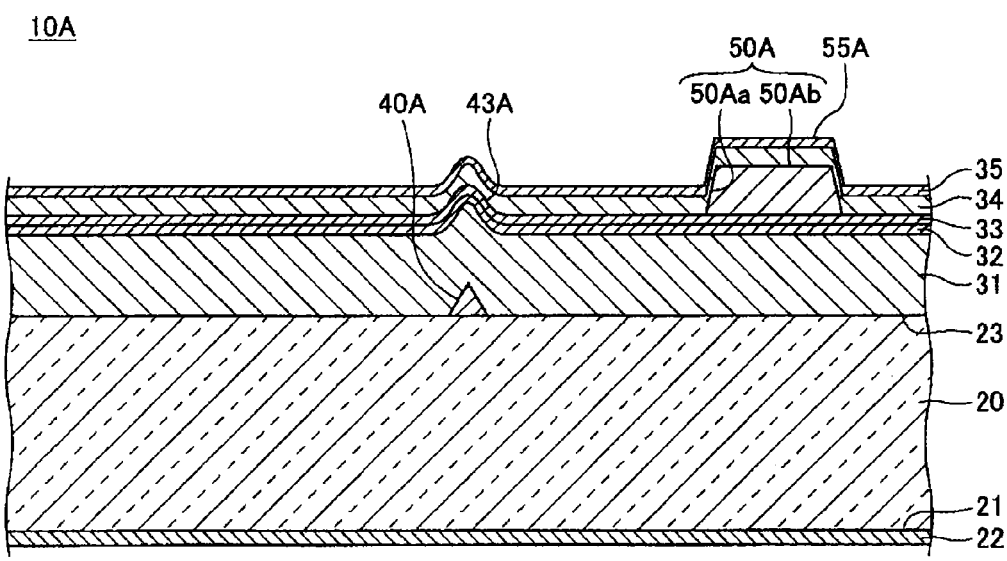
FIG. 9 is a cross-sectional view of a reflective mask blank according to the second embodiment of the present invention.

FIG. 9 is a cross-sectional view of the reflective mask blank 10A according to the second embodiment of the present invention. The reflective mask blank 10A has the convex-shaped temporary fiducial mark 40A and the convex-shaped fiducial mark 50A.

(Temporary Fiducial Mark)

The temporary fiducial mark 40A is formed in a convex shape on the surface 23 of the substrate 20. Before the formation of the multilayer reflective film 31, the position of the defect of the substrate 20 can be identified, based on the position of the temporary fiducial mark 40A as a reference position, and can be recorded on a recording medium.

On the planar view thereof (seen in the direction perpendicular to the surface 23 of the substrate 20), the shape of the convex-shaped temporary fiducial mark 40A is, for example, a square, triangular, circular, oval, rhombic or the like one, while on the side view thereof, the shape is, for example, a triangular as in FIG. 9, square, semi-circular or the like one.

Regarding the size of the convex-shaped temporary fiducial mark 40A, for example, on the planar view thereof, the maximum length is at most 200 nm, preferably at most 70 nm and more preferably at most 50 nm, and the minimum length is at least 10 nm and preferably at least 30 nm. The maximum height of the temporary fiducial mark 40A is at most 20 nm, preferably at most 10 nm and more preferably at most 5 nm. The minimum height of the temporary fiducial mark 40A is at least 1 nm and preferably at least 2 nm. The temporary fiducial mark 40A having a size that falls within the range can secure the detection sensitivity with a commercial automatic defect inspection apparatus (e.g., M7360 manufactured by Lasertec) for reflective mask blanks and glass substrates, which uses far-UV light or visible light as the light source, and in addition, since the detection spot is not so large as to worsen the detection position reproducibility, the detection position reproducibility of the mark can be kept good. Consequently, the position of the defect existing in the surface 23 of the substrate 20 can be identified with sufficient accuracy.

The convex-shaped temporary fiducial mark 40A is formed by stacking a prescribed material, for example, chromium, tantalum or the like, on the surface 23 of the substrate 20. The material of the temporary fiducial mark 40A may be formed in a film shape on the surface 23 of the substrate 20 and then may be removed through lithography; or the material may be locally deposited on the surface 23 of the substrate 20. For the latter case, it can be used a method where a suitable gas is selected depending on the material to be deposited, and in an atmosphere containing a metal compound with platinum, tungsten or the like (e.g., hexacarbonyltungsten) and a hydrocarbon compound (naphthalene, phenanthrene, etc.), the substrate is irradiated with ion beams or electron beams so as to promote the decomposition of the metal compound to thereby locally deposit a metal film of platinum, tungsten or the like on the substrate.

As the convex-shaped temporary fiducial mark 40A, it can also be used a real defect existing in the surface 23 of the substrate 20, for example, a projection defect such as a particle or the like adhering to the surface as derived from washing or from the environment.

The convex-shaped temporary fiducial mark 40A is transferred to the multilayer reflective film 31, the protective layer 32, the buffer layer 33, the absorber layer 34 and the low-reflection layer 35 formed on the substrate 20 in this order, as shown in FIG. 9.

The temporary fiducial mark 40A of the surface of the substrate 20 may be omitted. In a case of using a current optical defect inspection apparatus, the inspection sensitivity on the multilayer reflective film 31 is higher than on the substrate 20, and accordingly, the defect of the substrate 20 can be transferred to the multilayer reflective film 31 and can be therefore detected on the multilayer reflective film 31. In cases where a defect (e.g., foreign substance, flaw, pit) exists in the surface of the substrate on which the multilayer reflective film 31 is formed, the periodical structure of the multilayer reflective film 31 may be disordered and defects (so-called phase defects) would be thereby formed in the multilayer reflective film.

(Fiducial Mark)

The fiducial mark 50A is formed in a convex shape by stacking a prescribed material on the surface of the multilayer reflective film 31 or on the surface of the layers 32 or 33 formed between the multilayer reflective film 31 and the absorber layer 34 (in this embodiment, on the surface of the buffer layer 33).

The material for the fiducial mark 50A is selected so that the light reflectivity of the fiducial mark 50A could differ from that in the peripheral area thereof. The material for the fiducial mark 50A is not specifically limited, but for example, as a film-formable material with an existing apparatus, it can be used Si and Mo used for the multilayer reflective film, Ta, Cr, Pt, W, C as well as their oxides, nitrides and others used for the absorber layer. The fiducial mark 50A formed in a convex shape by stacking any of these materials has a lower EUV light reflectivity than the area around the mark. The difference (absolute value) between the reflectivity to the inspection light of the fiducial mark 50 and the reflectivity to the inspection light of the area around the fiducial mark 50 is preferably at least 0.2%, more preferably at least 0.5% and even more preferably at least 1.0%.

The material of the fiducial mark 50A may be formed in a film shape on the surface for forming the fiducial mark 50A thereon and then may be removed through lithography; or the material may be locally deposited on the surface for forming the fiducial mark 50A thereon. For the latter case, it can be used a method where a suitable gas is selected depending on the material to be deposited, and in an atmosphere containing a metal compound with platinum, tungsten or the like (e.g., hexacarbonyltungsten) and a hydrocarbon compound (naphthalene, phenanthrene, etc.), the substrate is irradiated with ion beams or electron beams so as to promote the decomposition of the metal compound to thereby locally deposit a metal film of platinum, tungsten or the like on the substrate.

The convex-shaped fiducial mark 50A is formed to have a shape for the intended use thereof. For example, the convex-shaped fiducial mark 50A is formed as a cross on the planar view thereof, like in the first embodiment. The point of intersection between the centerline in one linear part and the centerline in the remaining linear part is the reference point.

At least three convex-shaped fiducial marks 50A are formed on the surface for forming the fiducial marks 50A (in this embodiment, on the surface of the buffer layer 33). These at least three fiducial marks 50A are not arranged on one and the same line. Of these at least three reference points, one reference point is taken as the origin; and the line that connects the origin to another reference point is the X axis, while the line that connects the origin to the remaining one reference point is the Y axis. The X axis and the Y axis may be perpendicular to each other.

Preferably, the convex-shaped fiducial mark 50A has a step face 50Aa that is nearly perpendicular to the face of forming the fiducial mark 50A and an offset face 50Ab that is nearly parallel to the face of forming the fiducial mark 50A, in order that the edges of the mark can be sharp and the side wall angles thereof can be steep.

The height of the convex-shaped fiducial mark 50A may be suitably defined in accordance with the type and the thickness of the layer to be formed on the fiducial mark 50A. The height of the convex-shaped fiducial mark 50A is, for example, from 2 to 300 nm, preferably from 7 to 150 nm and more preferably from 40 to 120 nm.

Preferably, the fiducial mark 50A has a size detectable in observation at a low magnification, and the size thereof may be defined in accordance with the dimensional tolerance and the like of the reflective mask blank 10A. The dimensional tolerance of one side (152.0 mm) of a standard square reflective mask blank is ±0.1 mm. When the reflective mask blank is set in a prescribed apparatus (e.g., in an electron beam image-drawing apparatus), for example, the two sides of the reflective mask blank are pressed against pins for positioning. In this stage, the position of the fiducial mark 50A could move by ±0.1 mm in every reflective mask blank. Therefore, for detecting the position within a short period of time, it is desirable that the fiducial mark 50A has a size detectable in observation at a low magnification. In cases where the dimensional tolerance is ±0.1 mm, it is desirable that the area of the fiducial mark 50A on the planar view thereof is from 1 $\mu m^2$ to 1 $mm^2$. Each linear part of the cruciform fiducial mark 50A may be, for example, such that the width W thereof is from 0.2 to 10 $\mu m$ and the length L thereof is from 10 to 500 $\mu m$. In this case, the area of the fiducial mark 50 on the planar view thereof is from 3.96 $\mu m^2$ to 9900 $\mu m^2$.

The convex-shaped fiducial mark 50A is formed in the region not used in the later process (e.g., in the region not to be patterned in the production process for the reflective photomask), and for example, the mark is formed in the periphery of the face for forming thereon the fiducial mark 50A.

Like in the first embodiment, the convex-shaped fiducial mark 50A is formed after the formation of the multilayer reflective film 31, and therefore, the edges thereof are sharp and the side wall angles thereof are steep, as compared with those of the temporary fiducial mark 43A transferred to the face for forming thereon the fiducial mark 50A (see FIG. 9). In addition, the convex-shaped fiducial mark 50A has low reflectivity to the inspection light of EUV light, as compared with the multilayer reflective film 31 in the region around the fiducial mark 50A. Owing to these results, in defect inspection of the multilayer reflective film 31 with EUV light, the contrast between the fiducial mark 50A and the area around the mark is high and therefore the reproducibility of the detection position of the fiducial mark 50A is bettered. Consequently, the position of the defect of the multilayer reflective film 31 can be accurately identified on the basis of the position of the fiducial mark 50A as a reference position. In addition, by selecting such a material that differs in the reflectivity to far-UV light to visible light, it is possible to form a fiducial mark also having good detection position reproducibility in inspection with far-UV light to visible light.

Also like in the first embodiment, the convex-shaped fiducial mark 50A is formed after the formation of the multilayer reflective film 31 and is transferred to the absorber layer 34 or the like that is thinner (about ¼ or so) than the multilayer reflective film 31. Accordingly, the transferred fiducial mark 55A is to have nearly the same shape as that of the original fiducial mark 50A, therefore bettering the reproducibility of the detection position with the inspection light (e.g., electron beam, EUV light, far-UV light or visible light) and providing the following advantageous effects (1) and (2). (1) In the process for producing the reflective photomask 100, an electron beam image-drawing apparatus, a coordinate measuring apparatus and a mask appearance inspection apparatus can detect the position of the fiducial mark 55A with electron beam or far-UV light at good reproducibility. Accordingly, these apparatuses enable good and accurate detection of the position of the defect in the multilayer reflective film 31 and the like, based on the information provided by the supplier of the reflective mask blank 10A. (2) In inspection of the absorber layer 34 and the low-reflection layer 35, the position of the fiducial mark 55A can be detected at good producibility with far-UV light or visible light.

Third Embodiment

This embodiment relates to a method for producing the reflective mask blank 10 mentioned above. The same shall apply also to the production method for the reflective mask blank 10A.

Figure 10:
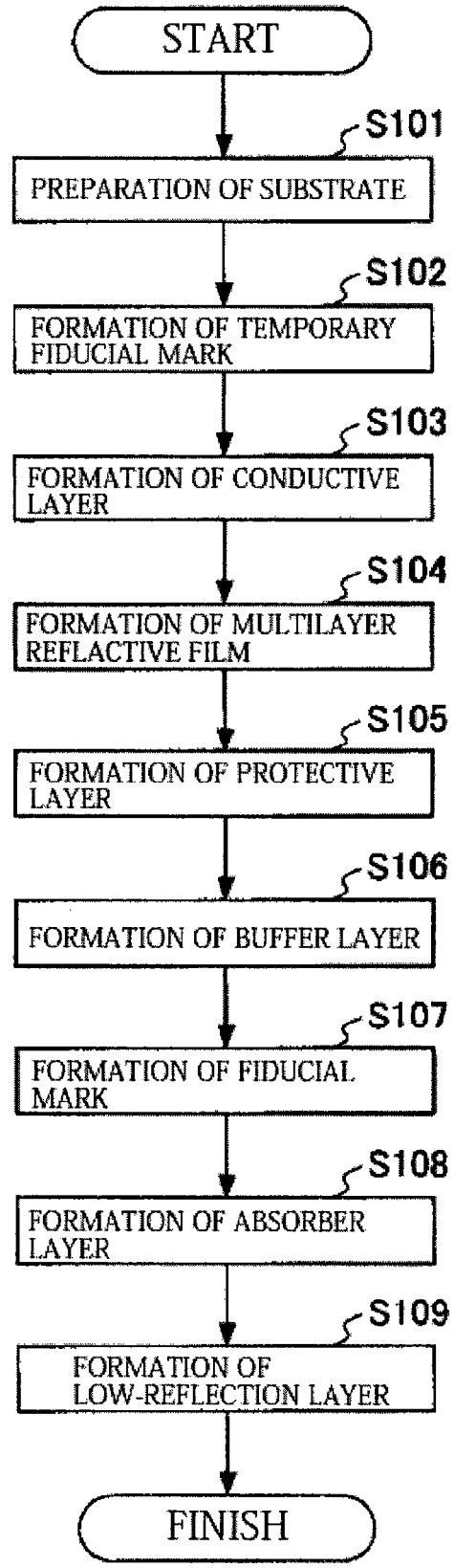
FIG. 10 is a flowchart of the method for manufacture of a reflective mask blank according to the third embodiment of the present invention.

FIG. 10 is a flowchart of the method for manufacture of the reflective mask blank according to the third embodiment of the present invention.

The production method for the reflective mask blank 10 contains the step S101 of preparing the substrate 20, the step S102 of forming the temporary fiducial mark 40 on the surface 23 of the substrate 20, and the step S103 of forming the conductive layer 22 on the back surface 21 of the substrate 20. The production method for the reflective mask blank 10 further contains the step S104 of forming the multilayer reflective film 31, the step S105 of forming the protective layer 32, the step S106 of forming the buffer layer 33, the step S107 of forming the fiducial mark 50, the step S108 of forming the absorber layer 34, and the step S109 of forming the low-reflection layer 35. The method may further include a washing step or a drying step between the steps S101 to S109.

The step S107 of forming the fiducial mark 50 may be carried out after the step S104 of forming the multilayer reflective film 31 but before the step S108 of forming the absorber layer 34, and for example, the step may be carried out between the step S105 of forming the protective layer 32 and the step S106 of forming the buffer layer 33.

The production method for the reflective mask blank 10 of this embodiment includes the step of forming the fiducial mark 50, therefore enjoying the advantageous effects that are described in the first embodiment. For example, the fiducial mark 50 differs from the area around it in the reflectivity to the inspection light for the multilayer reflective film (i.e., there exist a contrast therebetween) and the reproducibility of the detection position with the inspection light (e.g., EUV light, far-UV light or visible light) is good, and consequently, the position of the defect in the multilayer reflective film 31 can be identified accurately. In addition, since the fiducial mark 50 is transferred to the reflective mask blank 10 to have nearly the same shape on the latter, the transferred fiducial mark 55 betters the reproducibility of the detection position with the inspection light (e.g., electron beam, EUV light, far-UV light or visible light) and provides the following advantageous effects (1) and (2). (1) In the process for producing the reflective photomask 100, an electron beam image-drawing apparatus, a coordinate measuring apparatus and a mask appearance inspection apparatus can detect the position of the fiducial mark 55 with electron beam, far-UV light or visible light at good reproducibility. Accordingly, these apparatuses enable good and accurate detection of the position of the defect in the multilayer reflective film 31 and the like, based on the information provided by the supplier of the reflective mask blank 10. (2) In inspection of the absorber layer 34 and the low-reflection layer 35, the position of the fiducial mark 55 can be detected at good producibility with far-UV light or visible light.

The step S102 of forming the temporary fiducial mark 40 may be omitted. In this case, the concave-shaped or convex-shaped defect that exists in the surface 23 of the substrate 20 could act as the temporary fiducial mark.

The step S105 of forming the protective layer 32, the step S106 of forming the buffer layer 33 and the step S109 of forming the low-reflection layer 35 are optional steps, and may be omitted. The method for manufacturing the reflective mask blank 10 may have any other step of forming any other functional layer.

The step S103 of forming the conductive layer 22 may be carried out after the steps S104 to S109, and the order of those steps is not specifically limited.

Fourth Embodiment

This embodiment relates to a method for quality control for the reflective mask blank 10 mentioned above. The same shall apply also to the method for quality control for the above-mentioned reflective mask blank 10A.

Figure 11:
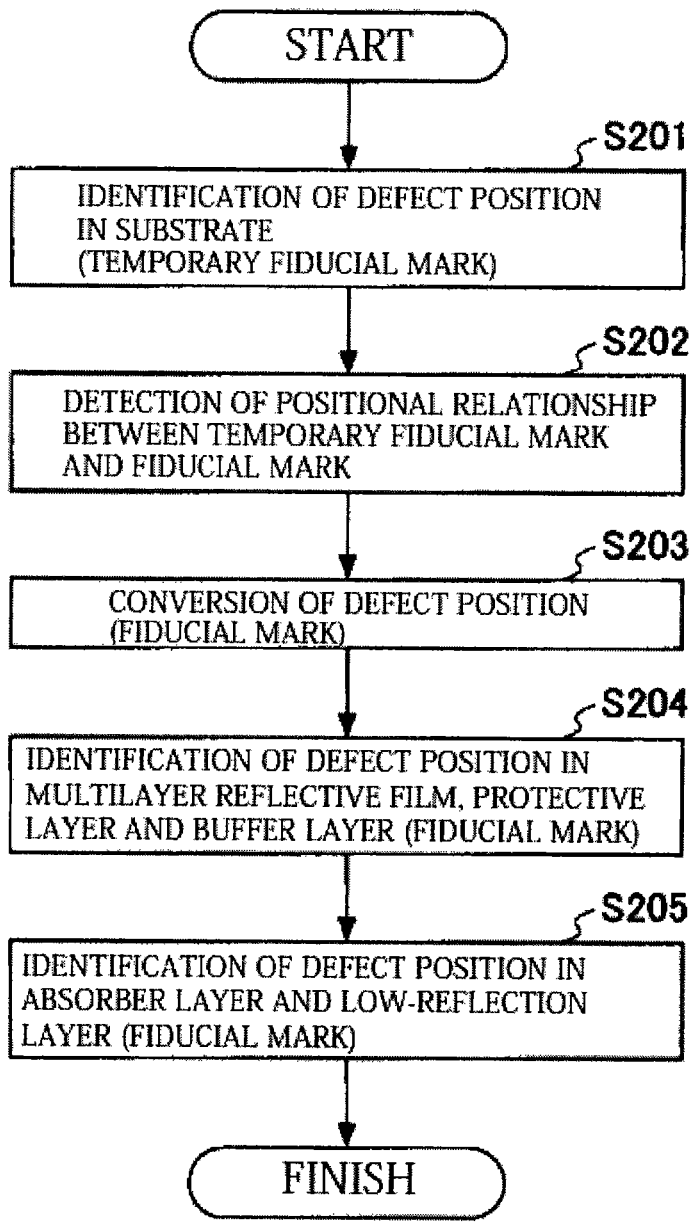
FIG. 11 is a flowchart of the method for quality control for a reflective mask blank according to the fourth embodiment of the present invention.

FIG. 11 is a flowchart of the method for quality control for the reflective mask blank according to the fourth embodiment of the present invention.

The method for quality control for the reflective mask blank 10 contains the first identification step S201 of identifying the defect position in the surface 23 of the substrate 20, based on the position of the temporary fiducial mark 40 as a reference position. The first identification step S201 is carried out after the step S102 of forming the temporary fiducial mark 40 (see FIG. 10) and before the step S104 of forming the multilayer reflective film 31 (see FIG. 10).

As the method of identifying the position of the defect, for example, there is mentioned a method of irradiating or scanning the surface 23 of the substrate 20 with spotlight of visible ray, UV ray, vacuum UV ray, soft X-ray or the like or with an electron beam, and then receiving the scattered light from the test sample to thereby detect the position of the temporary fiducial mark 40 and the position of the defect. In place of the scattered light, reflected light or transmitted light may also be used.

In the first identification step S201, the type of the defect (e.g., concave-shaped or convex-shaped) may be identified in addition to the position of the defect in the substrate 20. The information relating to the defect is recorded on a recording medium. In the presence of no defect, the information that indicates the presence of no defect is recorded on the recording medium.

The method for quality control for the reflective mask blank 10 further contains the detection step S202 of detecting the positional relationship between the position of the temporary fiducial mark 40 and the position of the fiducial mark 50, and the conversion step S203 of converting the position of the defect identified on the basis of the position of the temporary fiducial mark 40 as the reference position, into the position based on the position of the fiducial mark 50 as the reference position, on the basis of the positional relationship detected in the detection step S202. The converted results are recorded on a recording medium.

The detection step S202 is to detect the positional relationship between the position of the temporary fiducial mark 40, more precisely the position of the temporary fiducial mark 43 transferred to the layer (e.g., the buffer layer 33) formed on the temporary fiducial mark 40, and the position of the fiducial mark 50. The method for detecting the position of the temporary fiducial mark 40 and the position of the fiducial mark 50 is the same as the method for identifying the defect position mentioned above, and its description is omitted here. The detection step S202 may be carried out simultaneously with the second identification step S204 mentioned below.

The timing of the detection step S202 is not specifically limited. For example, the detection step S202 may be to detect, after the formation of the low-reflection layer 35, the positional relationship between the fiducial mark 55 transferred to the low-reflection layer 35 and the temporary fiducial mark also transferred to the low-reflection layer 35.

The conversion step S203 is to convert, for example, the position of the defect identified in the first identification step S201 into the position that is based on the position of the fiducial mark 50 as a reference position, on the basis of the positional relationship detected in the detection step S202. The results of conversion are recorded on a recording medium. The conversion step S203 may be carried out after the detection step S202, and the timing thereof is not specifically limited.

Further, the method for quality control for the reflective mask blank 10 contains the second identification step S204 of identifying the position of the defect in the multilayer reflective film 31 based on the position of the fiducial mark 50 as a reference position. The second identification step S204 is carried out after the step S107 of forming the fiducial mark 50 (see FIG. 10) and before the step S108 of forming the absorber layer 34 (see FIG. 10).

For example, the second identification step 202 is carried out after the step S106 of forming the buffer layer 33 to identify the position of the defect in the multilayer reflective film 31, the position of the defect in the protective layer 32 and the position of the defect in the buffer layer 33 all at a time. This is because the multilayer reflective film 31, the protective layer 32 and the buffer layer 33 are formed continuously in many cases.

The second identification step S204 in this embodiment is carried out after the step S106 of forming the buffer layer 33, to which, however, the present invention is not limited. For example, the step may be carried out before the step S105 of forming the protective layer 32, and the position of the defect in the multilayer reflective film 31 may be identified separately from the position of the defect in the protective layer 32 or the position of the defect in the buffer layer 33.

As the method of identifying the position of the defect, for example, there is mentioned a method of scanning the surface of the test sample (in this embodiment, the surface of the buffer layer 33) with spotlight of EUV light or the like, and then receiving the reflected light from the test sample to thereby detect the position of the fiducial mark 50 and the position of the defect.

In the second identification step S204, the type of the defect (e.g., concave-shaped or convex-shaped) may be identified in addition to the position of the defect of in the multilayer reflective film 31. The information relating to the defect is recorded on a recording medium. In the presence of no defect, the information that indicates the presence of no defect is recorded on the recording medium.

The method for quality control for the reflective mask blank 10 contains the third identification step S205 of identifying the position of the defect in the absorber layer 34 based on the position of the fiducial mark 50 as a reference position. The third identification step S205 is carried out after the step S108 of forming the absorber layer 34 (see FIG. 10).

For example, the third identification step S205 is carried out after the step S109 of forming the low-reflection layer 35 to identify the position of the defect in the absorber layer 34 and the position of the defect in the low-reflection layer 35 all at a time, based on the position of the fiducial mark 55 transferred to the low-reflection layer 35 as a reference position. This is because the absorber layer 34 and the low-reflection layer 35 are formed continuously in many cases.

The third identification step S205 in this embodiment is carried out after the step S109 of forming the low-reflection layer 35, to which, however, the present invention is not limited. For example, the step may be carried out before the step S109 of forming the low-reflection layer 35, and the position of the defect in the absorber layer 34 may be identified separately from the position of the defect in the low-reflection layer 35.

As the method of identifying the position of the defect, for example, there is mentioned a method of irradiating or scanning the surface of the test sample (in this embodiment, the surface of the low-reflection layer 35) with spotlight of visible light, UV light, EUV light or the like or with an electron beam, and then receiving the reflected light from the test sample to thereby detect the position of the fiducial mark 50 and the position of the defect.

In the third identification step S205, the type of the defect (e.g., concave-shaped or convex-shaped) may be identified in addition to the position of the defect in the absorber layer 34. The information relating to the defect is recorded on a recording medium. In the presence of no defect, the information that indicates the presence of no defect is recorded on the recording medium.

The information relating to the defects recorded on the recording medium in the first to third identification steps S201, S204 and S205 is used in the production step for the reflective photomask 100. The electron beam image-drawing apparatus, the coordinate measuring apparatus and the mask appearance inspection apparatus for use in the production step for the reflective photomask 100 can detect the reflected electron beam or the reflected UV ray to thereby detect the position of the fiducial mark 50 (precisely, the fiducial mark 55 transferred to the low-reflection layer 35) at good reproducibility, and based in the information provided by the supplier of the reflective mask blank 10, the defect position can be thereby known with accuracy.

The quality control method of this embodiment utilizes the fiducial mark 50 and therefore can enjoy the advantageous effects described in the first embodiment. For example, the fiducial mark 50 differs from the area around it in the reflectivity to the inspection light for the multilayer reflective film 31 (i.e., there exist a contrast therebetween) and the reproducibility of the detection position with the inspection light (e.g., EUV light, far-UV light or visible light) is good, and consequently, the position of the defect in the multilayer reflective film 31 can be identified accurately. In addition, since the fiducial mark 50 is transferred to the reflective mask blank 10 to have nearly the same shape on the latter, the transferred fiducial mark 55 betters the reproducibility of the detection position with the inspection light (e.g., electron beam, EUV light, far-UV light or visible light) and provides the following advantageous effects (1) and (2). (1) In the process for producing the reflective photomask 100, an electron beam image-drawing apparatus, a coordinate measuring apparatus and a mask appearance inspection apparatus can detect the position of the fiducial mark 55 with electron beam, far-UV light or visible light at good reproducibility. Accordingly, these apparatuses enable good and accurate detection of the position of the defect in the multilayer reflective film 31 and the like, based on the information provided by the supplier of the reflective mask blank 10. (2) In inspection of the absorber layer 34 and the low-reflection layer 35, the position of the fiducial mark 55 can be detected at good producibility with far-UV light or visible light.

The quality control method of this embodiment contains the first to third identification steps S201, S204 and S205, but it is sufficient to contain the second identification step S204. This is because the position of the defect in the multilayer reflective film 31 has the most significant influence on the quality of the reflective photomask 100.

Fifth Embodiment

In the above-mentioned first embodiment, the fiducial mark 50 is formed in the position separated from the temporary fiducial mark 40, on the planar view thereof. Different from this, in this embodiment, the fiducial mark is formed to overlap with the temporary fiducial mark. This embodiment is the same as the first embodiment except that there is a difference in the positioning of the temporary fiducial mark and the fiducial mark therebetween, and therefore the difference is described mainly.

Figure 12:
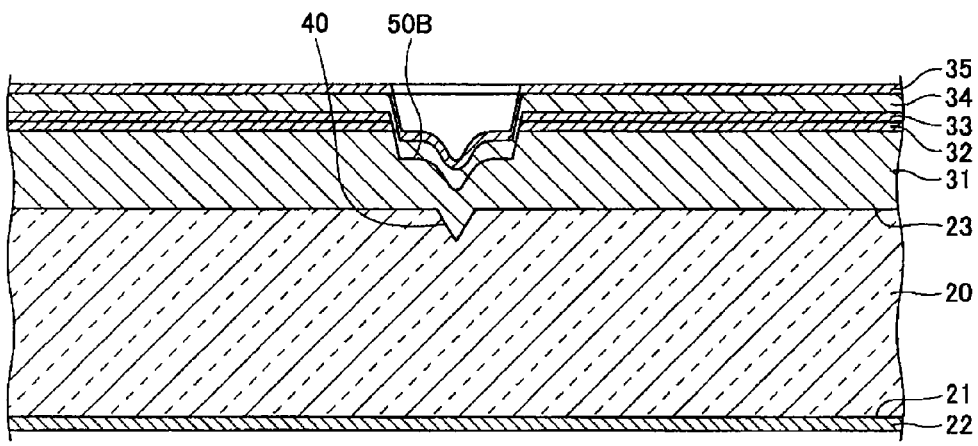
FIG. 12 is a cross-sectional view of a reflective mask blank according to the fifth embodiment of the present invention.

FIG. 12 is a cross-sectional view of the reflective mask blank according to the fifth embodiment of the present invention. The reflective mask blank 10B has the temporary fiducial mark 40 and the fiducial mark 50B.

The temporary fiducial mark 40 is formed in a concave shape or convex shape (in this embodiment, concave shape) on the surface 23 of the substrate 20. As the concave-shaped temporary fiducial mark 40, it can also be used a real defect existing in the surface 23 of the substrate 20, for example, a concave-shaped defect such as a pit or the like formed during polishing or washing and existing therein.

The fiducial mark 50B is formed in a concave shape or in a convex shape (in this embodiment, concave shape) on the face for forming thereon the fiducial mark 50B after the formation of the multilayer reflective film 31 and before the formation of the absorber layer 34. The concave-shaped fiducial mark 50B is formed by removing at least a part of the multilayer reflective film 31. Therefore, the mark provides the same advantageous effects as in the first embodiment.

On the planar view thereof, the fiducial mark 50B is formed to overlap with the temporary fiducial mark 40. Specifically, on the planar view thereof, the reference point of the fiducial mark 50B overlaps with the reference point of the temporary fiducial mark 40. Therefore, in the quality control process for the reflective mask blank of this embodiment, the detection step S202 (see FIG. 11) of detecting the positional relationship between the temporary fiducial mark and the fiducial mark and the conversion step S203 (see FIG. 11) that follows the detection step S202 are unnecessary.

The fiducial mark 50B is formed by removing a part of the multilayer reflective film 31, and therefore it is desirable that the mark satisfies at least one of the requirement that the size thereof, as seen from the top surface of the substrate, is larger than the size of the temporary fiducial mark 40 and the requirement that the depth of the fiducial mark 50B is larger than the depth of the temporary fiducial mark 40.

The first to fifth embodiments of the present invention are described above. However, the present invention is not limited to the above-mentioned embodiments. Various modifications and substitution may be added to the above-mentioned embodiments without departing from the scope of the present invention.

Figure 13:
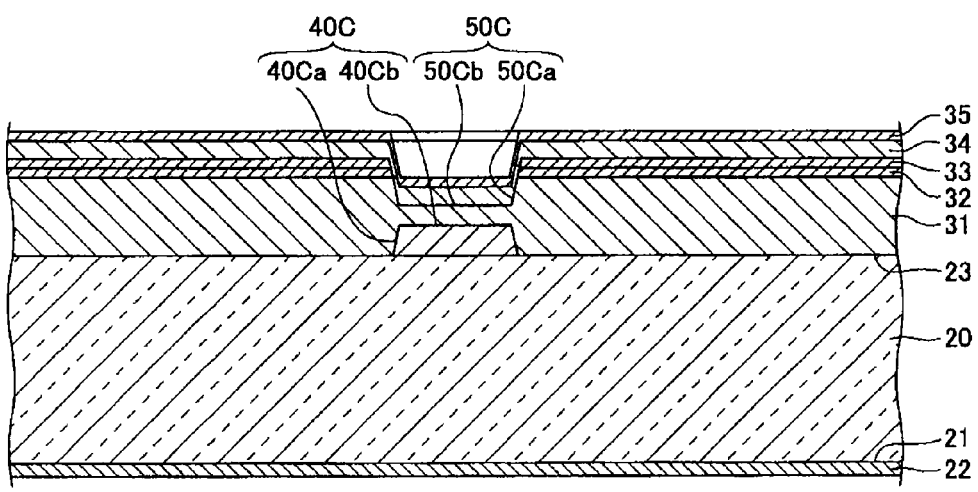
FIG. 13 is a cross-sectional view showing a modification example of FIG. 12.

For example, in the above-mentioned embodiments, the combination of the shape of the temporary fiducial mark (concave shape or convex shape) and the shape of the fiducial mark (concave shape or convex shape) is not specifically limited. FIG. 13 is a cross-sectional view showing a modification example of FIG. 12. The reflective mask blank 10C has the convex-shaped temporary fiducial mark 40C and the concave-shaped fiducial mark 50C. The convex-shaped temporary fiducial mark 40C has the step face 40Ca that is nearly perpendicular to the surface 23 of the substrate 20 and the offset face 40Cb that is nearly parallel to the surface 23 of the substrate 20. Similarly, the concave-shaped fiducial mark 50C has the step face 50Ca that is nearly perpendicular to the face for forming thereon the fiducial mark 50C (the surface of the buffer layer 33) and the offset face 50Cb that is nearly parallel to the face for forming thereon the fiducial mark 50C. On the planar view thereof, the profile of the offset face 40Cb overlaps with the profile of the offset face 50Cb. In this case, the multilayer reflective film 31 is thinner in the position of the fiducial mark 50C, and therefore the contrast between the fiducial mark 50C and the area around it is higher in inspection of the defect in the multilayer reflective film 31. Accordingly, the reproducibility of the detection position of the fiducial mark 50C betters.

EXAMPLES

Methods for producing the elements that constitute the reflective mask blank of the present invention are described. First, as the substrate for film formation thereon, a glass substrate of $SiO_2$—$TiO_2$ type, having a planar dimension of 152.4 mm×152.4 mm and a thickness of 6.3 mm was used. The glass substrate had a coefficient of thermal expansion of $0.2×10^{-7}/°C.$, a Young's modulus of 67 GPa, a Poisson ratio of 0.17 and a specific rigidity of $3.07×10^7$ $m^2/s^2$, and was polished so that the surface roughness of the main surface thereof could be at most 0.15 nm rms, and the degree of flatness thereof could be at most 100 nm.

Next, on one side (the back surface side) of the glass substrate, a film containing Cr as a main component was formed by a magnetron sputtering method to have a thickness of about 100 nm, thereby providing a conductive film having a sheet resistance of 100 Ω/square. Via the formed conductive film, the substrate was fixed to a tabular electrostatic chuck, and on the other side thereof opposite to the conductive film, a Mo film 2.3 nm and a Si film 4.5 nm were alternately formed in repetitive 50 cycles by an ion beam sputtering method, thereby giving a multilayer reflective film (Mo/Si multilayer reflective film) having a total thickness of 340 nm ((2.3 nm+4.5 nm)×50). The uppermost layer of the Mo/Si multilayer reflective film is a Si film.

The Mo film was formed by using a Mo target in a sputtering gas atmosphere of Ar (gas pressure: 0.02 Pa) with an applied voltage of 700 V at a film formation speed of 3.84 nm/min, thereby having a thickness of 2.3 nm. The Si film was formed by using a boron-doped Si target in a sputtering gas atmosphere of Ar (gas pressure: 0.02 Pa) with an applied voltage of 700 V at a film formation speed of 4.62 nm/min, thereby having a thickness of 4.5 nm.

Next, a protective layer of Ru was formed by an ion beam sputtering method. The Ru layer was formed by using a Ru target in a sputtering gas atmosphere of Ar (gas pressure: 0.02 Pa) with an applied voltage of 700 V at a film formation speed of 3.12 nm/min, thereby having a thickness of 2.5 nm. The reflective mask blank of this Example does not require any specific buffer layer since the Ru layer is used as the protective layer.

Next, an absorber layer of TaN was formed on the protective film by a magnetron sputtering method. The TaN layer was formed by using a Ta target in a mixed gas of Ar and $N_2$ (Ar: 86 vol %, $N_2$: 14 vol %, gas pressure: 0.3 Pa) with an inputted power of 150 W at a film formation speed of 7.2 nm/min, thereby having a thickness of 60 nm.

Finally, a low-reflection layer of TaON was formed on the absorber layer by a magnetron sputtering method. The TaON layer was formed by using a Ta target in a mixed gas of Ar, $O_2$ and $N_2$ (Ar: 49 vol %, $O_2$: 37 vol %, $N_2$: 14 vol %, gas pressure: 0.3 Pa) with an inputted power of 250 W at a film formation speed of 2.0 nm/min, thereby having a thickness of 8 nm.

On the surface of the substrate or the surface after the film formation in the reflective mask blank produced according to the above-mentioned production method, formed was a cruciform fiducial mark according to the condition shown in the Table given below. The length L of the fiducial mark, as referred to in FIG. 4, was 500 μm in every Example shown below (Example 1 to Example 13).

TABLE 1

| No. | Fiducial Mark Forming Face | Temporary Fiducial Mark | Cross-Sectional Profile of Fiducial Mark | Width W of Fiducial mark [nm] | Depth/Height of Fiducial Mark [nm] |
|---|---|---|---|---|---|
| Example 1 | surface of glass substrate | no | concave | 5000 | 20 |
| Example 2 | surface of glass substrate | no | concave | 5000 | 40 |
| Example 3 | surface of glass substrate | no | concave | 5000 | 80 |
| Example 4 | surface of glass substrate | no | concave | 5000 | 120 |
| Example 5 | surface of Ru layer | no | concave | 5000 | 5 |
| Example 6 | surface of Ru layer | no | concave | 5000 | 40 |
| Example 7 | surface of Ru layer | no | concave | 5000 | 80 |
| Example 8 | surface of Ru layer | no | concave | 1000 | 80 |
| Example 9 | surface of TaON layer | yes | concave | 5000 | 20 |
| Example 10 | surface of TaON layer | yes | concave | 5000 | 40 |
| Example 11 | surface of TaON layer | yes | concave | 5000 | 80 |
| Example 12 | surface of TaON layer | yes | concave | 1000 | 80 |
| Example 13 | surface of Ru layer | no | convex | 5000 | 80 |

Example 1 to Example 4

In Example 1 to Example 4, a cruciform concave-shaped fiducial mark having a width W of 5000 nm and a length of 500 μm and having a depth varying within a range of from 20 to 120 nm was formed on the surface of glass by a focused ion beam method. Subsequently, according to the above-mentioned production method, the multilayer reflective film, the protective layer, the absorber layer and the low-reflection layer were formed to produce the reflective mask blank. When a visible laser defect inspection apparatus (M1350 manufactured by Lasertec) was applied to the reflective mask blank produced herein, the fiducial mark formed was detected. However, when an electron beam image-drawing apparatus (acceleration voltage: 50 kV) was used, the fiducial mark-derived signal was weak and was difficult to detect.

Example 5 to Example 8

In Example 5 to Example 8, a cruciform concave-shaped fiducial mark having a width W of 5000 nm and a length of 500 µm and having a depth varying within a range of from 5 to 80 nm was formed on the surface of the protective layer of Ru layer, by a focused ion beam method. The Ru protective layer had a thickness of 2.5 nm, and therefore in all Example 5 to Example 8, the Mo/Si multilayer reflective film was etched to a given depth.

Subsequently, according to the above-mentioned production method, the absorber layer and the low-reflection layer were formed to produce the reflective mask blank. When a defect inspection apparatus (M1350 manufactured by Lasertec) was applied to the reflective mask blank produced herein, the fiducial mark formed was detected, and also when an electron beam image-drawing apparatus (acceleration voltage: 50 kV) was used, the fiducial mark was detected, and reproducibility of the mark detection position was good.

Example 9 to Example 12

In Example 9 to Example 12, a temporary fiducial mark was formed on the surface of the glass substrate, and subsequently, the multilayer reflective film, the protective layer, the absorber layer and the low-reflection layer were formed. A cruciform concave-shaped fiducial mark having a width W shown in Table 1 and having a depth varying within a range of from 20 to 80 nm was formed on the surface the low-reflection layer of TaON layer, by a focused ion beam method to produce the reflective mask blank.

When a defect inspection apparatus (M1350 manufactured by Lasertec) was applied to the reflective mask blank produced herein, the fiducial mark formed was detected, and also when an electron beam image-drawing apparatus (acceleration voltage: 50 kV) was used, the fiducial mark was detected, and reproducibility of the mark detection position was on the same level as that for the mark on the surface of the protective layer. However, in the case where the fiducial mark formed on the low-reflection layer is referred to, the defect on the multilayer reflective film, as connected with the temporary fiducial mark, must be checked up in relation to the coordinates of the fiducial mark on the low-reflection layer, and in the case, therefore, the step may worsen the position accuracy. Consequently, as compared with that in the case of forming fiducial mark on the multilayer reflective film, the position accuracy in this case may worsen.

Example 13

In Example 13, a cruciform convex-shaped fiducial mark having a width W shown in Table 1 and having a height of 80 nm is formed on the surface the protective layer of Ru layer. Concretely, a Cr film is formed on the surface of the Ru layer by a magnetron sputtering method to have a thickness of 80 nm, and a negative resist for electron beams is applied thereon and dried, and a cruciform mark pattern is formed by an electron beam. In the subsequent development step, the resist is removed except the electron beam pattern. Subsequently, the Cr film is removed by dry etching, and then the resist on the electron beam pattern is peeled off. Thereafter, according to the above-mentioned production method, the absorber layer and the low-reflection layer is formed to produce the reflective mask blank.

When a defect inspection apparatus (M1350 manufactured by Lasertec) to the fiducial mark formed in the reflective mask blank produced herein, the fiducial mark formed is detected, and also when an electron beam image-drawing apparatus (acceleration voltage: 50 kV) is used, the fiducial mark is detected, and can be confirmed to be useful as a fiducial mark.

While the present invention has been described in detail and with reference to specific embodiments thereof, it will be apparent to one skilled in the art that various changes and modifications can be made therein without departing from the spirit and scope thereof.

The present application is based on Japanese Patent Application 2011-191057 filed on Sep. 1, 2011, and its contents are herein incorporated by reference.

DESCRIPTION OF REFERENCE NUMERALS AND SIGNS

10 Reflective Mask Blank
20 Substrate
31 Multilayer Reflective Film
32 Protective Layer
33 Buffer Layer
34 Absorber Layer
35 Low-Reflection Layer
40 Temporary Fiducial Mark
50 Fiducial Mark
100 Reflective Photomask

The invention claimed is:

1. A reflective mask blank, comprising:
   a substrate;
   a multilayer reflective film formed on the substrate and configured to reflect exposure light; and
   an absorber layer formed on the multilayer film and configured to absorb the exposure light,
   wherein the multilayer reflective film has a concave structure forming a fiducial mark indicating a reference position of the multilayer reflective film, and the concave structure is formed on a surface of the multilayer reflective film such that the concave structure has a concaved surface of a multilayer reflective portion of the multilayer reflective film and that a reflectivity of the concaved surface of the multilayer reflective film is different from an area surrounding the concave structure with respect to a light with a prescribed wavelength.

2. The reflective mask blank according to claim 1, wherein the concave structure has the concaved surface of the multilayer reflective film formed by removing a portion of the multilayer reflective film.

3. The reflective mask blank according to claim 2, further comprising:
   a layer formed between the multilayer reflective film and the absorber layer,
   wherein the concave structure is formed by removing a portion of the layer formed between the multilayer reflective film and the absorber layer.

4. The reflective mask blank according to claim 2, wherein the concave structure has a bottom portion comprising a material which differs from a material of an uppermost layer of the multilayer reflective film.

5. The reflective mask blank according to claim 1, wherein the exposure light is EUVL.

6. The reflective mask blank according to claim 1, further comprising:
   a protective layer formed between the multilayer reflective film and the absorber layer, wherein a portion of absorber layer is formed on the concaved surface of the multilayer reflective film.

7. The reflective mask blank according to claim 3, wherein the layer formed between the multilayer reflective film and the absorber layer is at least one of a protective layer and a buffer layer.

8. A method for quality control for a reflective mask blank described in claim 1, the method comprising:
identifying a position of a defect in the multilayer reflective film based on a position of the fiducial mark after formation of the multilayer reflective film and before formation of the absorber layer.

9. The method for quality control for a reflective mask blank according to claim 8, further comprising:
identifying a position of a defect on the substrate based on a position of a temporary fiducial mark existing on the substrate;
detecting a positional relationship between the temporary fiducial mark and the fiducial mark; and
converting the position of the defect identified based on the position of the temporary fiducial mark as a reference position into a position based on the position of the fiducial mark as a reference position based on the positional relationship.

10. The method for quality control for a reflective mask blank according to claim 8, further comprising:
identifying a position of a defect on the substrate based on a position of a concave-shaped or convex-shaped temporary fiducial mark existing on the substrate,
wherein the fiducial mark is formed in a position overlapping with the temporary fiducial mark in a planar view.

11. The method for quality control for a reflective mask blank according to claim 9, wherein the temporary fiducial mark has a concave shape or a convex shape.

12. A reflective mask blank, comprising:
a substrate;
a multilayer reflective film formed on the substrate and configured to reflect exposure light;
an absorber layer formed on the multilayer film and configured to absorb the exposure light; and
a convex structure formed on the multilayer reflective film such that the convex structure is forming a fiducial mark indicating a reference position of the multilayer reflective film,
wherein the convex structure is formed such that a reflectivity of the convex structure is different from an area surrounding the convex structure with respect to a light with a prescribed wavelength.

13. The reflective mask blank according to claim 12, wherein the exposure light is EUVL.

14. The reflective mask blank according to claim 12, wherein the convex structure comprises a material stacked on a surface of the multilayer reflective film or a surface of a layer formed between the multilayer reflective film and the absorber layer.

15. A method for producing a reflective mask blank, comprising:
forming a concave structure or a convex structure on a surface of a multilayer reflective film or on a surface of a layer formed between the multilayer reflective film and an absorber layer such that the concave structure or the convex structure forms a fiducial mark indicating a reference position of the multilayer reflective film,
wherein the multilayer reflective film is formed on a substrate and is configured to reflect exposure light, the absorber layer is formed on the multilayer film and is configured to absorb the exposure light, the concave structure is formed on the surface of the multilayer reflective film such that the concave structure has a concaved surface of a multilayer reflective portion of the multilayer reflective film, and the concave structure or the convex structure is formed such that a reflectivity of the concave structure or the convex structure is different from an area surrounding the concave structure or the convex structure with respect to a light with a prescribed wavelength.

16. The method for manufacturing a reflective mask blank according to claim 15, wherein the concave structure has the concaved surface of the multilayer reflective film formed by removing a portion of the multilayer reflective film.

17. The method for manufacturing a reflective mask blank according to claim 16, further comprising:
a layer formed between the multilayer reflective film and the absorber layer,
wherein the concave structure is formed by removing a portion of the layer formed between the multilayer reflective film and the absorber layer.

18. The method for manufacturing a reflective mask blank according to claim 16, wherein the concave structure has a bottom portion comprising a material which differs from a material of an uppermost layer of the multilayer reflective film.

19. The method for manufacturing a reflective mask blank according to claim 18, wherein the convex structure is formed by stacking a prescribed material on the surface of the multilayer reflective film or on the surface of the layer formed between the multilayer reflective film and the absorber layer.

20. The method for manufacturing a reflective mask blank according to claim 15, wherein the exposure light is EUVL.

* * * * *